US010894121B2

(12) United States Patent
Cheng et al.

(10) Patent No.: US 10,894,121 B2
(45) Date of Patent: *Jan. 19, 2021

(54) SMALL MOLECULE DYE FOR MOLECULAR IMAGING AND PHOTOTHERMAL THERAPY

(71) Applicant: The Board of Trustees of the Leland Stanford Junior University, Stanford, CA (US)

(72) Inventors: Zhen Cheng, Stanford, CA (US); Xuechuan Hong, Wuhan (CN); Hongjie Dai, Cupertino, CA (US); Hao Chen, Wuhan (CN); Alexander Antaris, Stanford, CA (US); Kai Cheng, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 16/186,947

(22) Filed: Nov. 12, 2018

(65) Prior Publication Data
US 2019/0192761 A1    Jun. 27, 2019

Related U.S. Application Data

(62) Division of application No. 15/051,563, filed on Feb. 23, 2016, now Pat. No. 10,124,111.

(60) Provisional application No. 62/120,290, filed on Feb. 24, 2015.

(51) Int. Cl.
A61B 5/00       (2006.01)
A61B 8/00       (2006.01)
A61B 10/00      (2006.01)
A61M 5/00       (2006.01)
C07K 14/765     (2006.01)
A61K 49/00      (2006.01)
A61K 41/00      (2020.01)
A61K 49/22      (2006.01)
C09B 57/00      (2006.01)
A61K 47/60      (2017.01)
A61K 31/433     (2006.01)

(52) U.S. Cl.
CPC ......... A61M 5/007 (2013.01); A61K 41/0052 (2013.01); A61K 47/60 (2017.08); A61K 49/0021 (2013.01); A61K 49/0052 (2013.01); A61K 49/0054 (2013.01); A61K 49/0056 (2013.01); A61K 49/22 (2013.01); C07K 14/765 (2013.01); C09B 57/008 (2013.01); A61B 5/0095 (2013.01); A61K 31/433 (2013.01)

(58) Field of Classification Search
None
See application file for complete search history.

(56) References Cited

U.S. PATENT DOCUMENTS 6,534,041 B1    3/2003  Licha et al.
10,124,111 B2 * 11/2018  Cheng ............... C07K 14/765
2009/0087493 A1  4/2009  Dai et al.
2013/0230464 A1  9/2013  Yi et al.

OTHER PUBLICATIONS

Ajayaghosh, A., et al., "Donor-acceptor type low band gap polymers: polysquaraines and related systems," Chem. Soc. Rev. (2003) 32:181-191.
Diao, S., et al., "Biological imaging without autofluorescence in the second near-infrared window," Nano. Res. (2015) 8(9):3027-3034.
Hirsch, L.R., et al., "Nanoshell-mediated near-infrared thermal therapy of tumors under magnetic resonance guidance," PNAS (2003) 100(23):13549-13554.
Hong, G., et al., "In Vivo Fluroescence Imaging with Ag2S Quantum Dots in the Second Near-Infrared Region," Angew. Chem. (2012) 124:9956-9959.
Hong, G., et al., "Multifunctional in vivo vascular imaging using near-infrared II fluorescence," Nat. Med, (2012) 18:1841-1846.
Hong, G., et al., "Near-Infrared-Fluorescence-Enhanced Molecular Imaging of Live Cells on Gold Substrates," Angew. Chem. Int. Ed. (2011) 50:4644-4648.

(Continued)

Primary Examiner — Michael G. Hartley
Assistant Examiner — Melissa J Perreira
(74) Attorney, Agent, or Firm — Brian E. Davy; Michael J. Blessent; Bozicevic, Field & Francis LLP

(57) ABSTRACT

Disclosed is a small molecule dye for use in imaging in the near-infrared window, namely between 1000 nm-1700 nm wavelength. The present dyes are also useful for photoacoustic imaging and photothermal therapy. The dyes have a structure of a D-A-D (donor-acceptor-donor) fluorescent compound core and side chains rendering the compounds water soluble and easily conjugated to hydrophilic polymers and/or targeting ligands. Further disclosed is compound, CH1055 that can be PEGylated, conjugated to a targeting ligand, or conjugated to taurine. Key steps utilized to assemble the core structure of the target included a cross-Suzuki coupling reaction, iron reduction and N-thionylaniline induced ring closure. Four carboxylic acid groups were introduced into the donor-acceptor-donor (D-A-D) type fluorescent compound to impart a certain aqueous solubility and to allow facile conjugation to targeting ligands.

16 Claims, 12 Drawing Sheets
Specification includes a Sequence Listing.

(56) References Cited

OTHER PUBLICATIONS

Hong, G., et al., "Near-Infrared II Fluorescence for Imaging Hindlimb Vessel Regeneration With Dynamic Tissue Perfusion Measurement" Circ. Cardiovasc. Imaging (2014) 7(3):517-525.

Hong, G., et al., "Ultrafast fluorescence imaging in vivo with conjugated polymer fluorophores in the second near infrared window," Nat. Commun. (2014) 5:4206, 9 pp.

Qian, G., et al., "Band Gap Tunable, Donor-Acceptor-Donor Charge-Transfer Heteroquinoid-Based Chromophores: Near Infrared Photoluminescence and Electroluminescence" Chem. Mater. (2008) 20:6208-6216.

* cited by examiner

3A

3B

SEQUENCE LISTING

```
<160> NUMBER OF SEQ ID NOS: 1

<210> SEQ ID NO 1
<211> LENGTH: 59
<212> TYPE: PRT
<213> ORGANISM: Artificial
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (59)..(59)
<223> OTHER INFORMATION: AMIDATION

<400> SEQUENCE: 1

Cys Val Asp Asn Lys Phe Asn Lys Glu Met Trp Ala Ala Trp Glu Glu
1               5                   10                  15

Ile Arg Asn Leu Pro Asn Leu Asn Gly Trp Gln Met Thr Ala Phe Ile
            20                  25                  30

Ala Ser Leu Val Asp Asp Pro Ser Gln Ser Ala Asn Leu Leu Ala Glu
            35                  40                  45

Ala Lys Lys Leu Asn Asp Ala Gln Ala Pro Lys
        50                  55
```

SMALL MOLECULE DYE FOR MOLECULAR IMAGING AND PHOTOTHERMAL THERAPY

CROSS-REFERENCE TO RELATED APPLICATIONS

This application claims priority from U.S. Provisional Patent Application No. 62/120,290 filed on Feb. 24, 2015, which is hereby incorporated by reference in its entirety.

STATEMENT OF GOVERNMENTAL SUPPORT

This invention was made with Government support under contract DE-SC0008397 awarded by the United States Department of Energy. The Government has certain rights in the invention.

REFERENCE TO SEQUENCE LISTING, COMPUTER PROGRAM, OR COMPACT DISK

This application contains a Sequence Listing which has been submitted as an ASCII text file and is hereby incorporated by reference in its entirety. This text file was created on Jan. 20, 2016, is named 3815_126_1_seq_list.txt, and is 1,178 bytes in size.

BACKGROUND OF THE INVENTION

Field of the Invention

The present invention relates to the field of molecular imaging and therapy, in particular to the field of photothermal therapy, photoacoustic imaging and fluorescent imaging of biological systems in the near-infrared-II window and the synthesis and modification of an NIR fluorescent dye having an emission peak in the NIR-II spectrum.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Fluorescence imaging in the near-infrared (NIR) window near 800 nm has been used in clinical procedures ranging from the assessment of vascular flow in grafted tissue during reconstructive surgery to retinal angiography for the diagnosis of retinal detachments or macular degeneration.(1, 2) Fluorescent imaging has a wide range of benefits not afforded by other imaging modalities derived from its combination of high spatial and temporal resolution.(3-6) Currently there are only two clinically approved NIR fluorophores, indocyanine green (ICG) and methylene blue (MB), both of which are small molecules that are rapidly excreted. (7) Their fluorescence emission lies within the first near-infrared window (NIR-I=750-900 nm). While imaging within this region is far superior compared to visible wavelengths, recent work has demonstrated a dramatic improvement in imaging quality when using fluorophores emitting within the second near-infrared window (NIR-II=1000-1700 nm).(5, 8-10) Diminished tissue autofluorescence, reduced photon scattering, and low levels of photon absorption when imaging at progressively longer wavelengths allows for centimeters imaging depth at low resolution and micron-scale resolution of anatomic features (up to ~3 mm depth or even ~1 cm depth in some cases) that are otherwise unresolvable within the traditional NIR-I region (~0.2 mm depth).(5, 11, 12)

Thus far, inorganic nanomaterials comprise the majority of NIR-II fluorophores as their highly tunable electronic structures can produce low band-gap semiconductors that emit long-wavelength photons. While a key characteristic of an imaging contrast agent for clinical use is its ability for rapid excretion due to unknown long term toxicity concerns, to date all NIR-II contrast agents are excreted slowly and are largely retained within the organs of the reticuloendothelial system (RES) such as the liver and spleen.(8, 13-18) Furthermore, due to synthetic limitations, all current molecular NIR-II fluorophores must be encapsulated in a polymer matrix due to their high hydrophobicity, which significantly increases their size past the renal filtration threshold of ~40 kD.(19) Like ICG in the NIR-I window, a contrast agent based on a second near-infrared window small molecule fluorophore with favorable excretion pharmacokinetics and minimal cellular toxicity would facilitate FDA approval and clinical translation of NIR-II imaging.

Fluorescent imaging can help to pinpoint tumor locations near the skin's surface in a variety of cancers, such as head and neck, melanoma, and breast cancer.(20) The main approaches to fluorescently labelling tumors are through both non-specific means that utilize the enhanced permeability and retention (EPR) effect as well as molecular imaging that employs specific targeting ligands to label unique features on cancerous cells.(21) As the maximum fluorescent signal strength of a tumor is often dictated by parameters, such as the receptor-ligand binding kinetics, the permeation of the imaging agent into a given tissue, and the imaging agent's optical properties, reduction in background autofluorescence in the NIR-II window could be critical to achieving a high signal-to-background ratio (SBR) for pinpointing tumors.(3) Furthermore, imaging in the NIR-II offers other notable benefits when compared to the NIR-I, such as significant improvements in spatial resolution and imaging depth due to the reduction in scattering at longer wavelengths.(5, 8) Great improvements can be obtained in in vivo imaging metrics such as the tumor-to-normal tissue (T/NT) ratio by using a fluorophore emitting within the NIR-II to take advantage of the negligible background autofluorescence and minimal scattering within this region.

There is currently a need to develop imaging agents that are not toxic and can emit in the NIR-II region. Such agents are particularly desired for use in the clinic, where they could benefit patients needing diagnosis or treatment of diseases such as cancer.

Related Patents and Publications

Hong et al., "Ultrafast fluorescence imaging in vivo with conjugated polymer fluorophores in the second near-infrared window," Nature Communications 5, 4206, published 20 Jul. 2014 discloses non-covalent functionalization with phospholipid-polyethylene glycol that results in water-soluble and biocompatible polymeric nanoparticles, allowing for live cell molecular imaging at >1,000 nm with polymer fluorophores. The polymer poly(benzo[1,2-b:3,4-b]difuran-alt-fluorothieno-[3,4-b]thiophene) was used.

Qian et al., "Band Gap Tunable, Donor-Acceptor-Donor Charge-Transfer Heteroquinoid-Based Chromophores: Near-infrared Photoluminescence and Electroluminescence," Chem. Mater., 2008, 20 (19), pp 6208-6216, discloses a series of D-π-A-π-D type of near-infrared (NIR) fluorescent compounds based on benzobis(thiadiazole) and its selenium analogues. All-organic light-emitting diodes based on several of the disclosed compounds were made. The compounds were not shown to be modifiable with a conjugating group, and were tested in organic solvent.

BRIEF SUMMARY OF THE INVENTION

The following brief summary is not intended to include all features and aspects of the present invention, nor does it imply that the invention must include all features and aspects discussed in this summary.

In general, the present invention comprises preparation of novel small molecule dyes for use in NIR II (100-1700 nm) imaging, photoacoustic imaging and photothermal therapy in biological systems such as whole bodies and tissues. The dyes are modified by a hydrophilic polymer or by a small molecule like taurine or other sulfonic acids and thereby have high in vivo biocompatibility and can be rapidly excreted without causing toxicity. In other aspects, the present invention comprises methods for producing images with high resolution of internal features using an NIR light source and detecting fluorescence, acoustic signals and/or thermal effects in a two dimensional array.

The present invention comprises, in certain embodiments, a near-infrared (NIR-II range) fluorophore having a structure of:

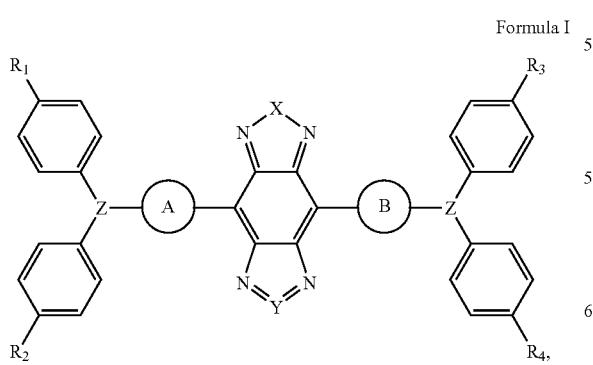

Formula I wherein

A and B are independently selected from the group consisting of

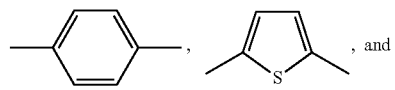
, and

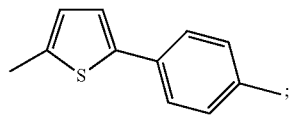
;

X and Y are each independently selected from the group consisting of S and Se;

Z is independently one of N and P; and

R1, R2, R3 and R4 are each independently of the formula -alkyl-linker, wherein alkyl is $-(CH_2)_n-$, further wherein n is an integer between 1 and 14, inclusive and wherein linker is selected from one of (i) sulfonic, phosphonic, carboxyl, hydroxyl, NHS-ester, maleimide, amine, —SH, —SO3, and hydrazide. In certain embodiments, R1, R2, R3 and R4 are independently each one of i) -alkyl-polymer, wherein "alkyl" is —(CH2)n-, further wherein n is between one of 1 and 14, inclusive, and further wherein "polymer" is a polymer of the group consisting of ethylene glycol (EG), methacrylic acid (MA), 2-hydroxyethyl methacrylate (HEMA), ethyl acrylate (EA), 1-vinyl-2-pyrrolidinone (VP), propenoic acid 2-methyl ester (PAM), monomethacryloyloxyethyl phthalate, (EMP) and ammonium sulphatoethyl methacrylate (SEM), having the formula -alkyl-polymer; (ii) a radical consisting of the group of  $-(CH_2)_2C(=O)-NH(CH_2)_2SO_3H-NH(CH_2)SO_3H$ and (iii) R1, R2, and R3 are each lower alkyl acid, and R4 is of the formula

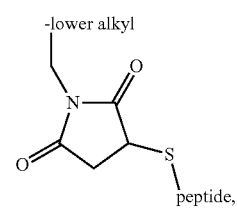

wherein "lower alkyl" has a structure of a 6 carbon chain and "peptide" has a structure of an Fv fragment, a single-chain Fv, a diabody, or an affibody molecule.

In certain aspects, the invention comprises a compound as described above wherein R1, R2, R3 and R4 are each 3-phenylpropanoic acid or a 3-phenyl lower alkyl acid.

In certain aspects, the invention comprises a compound as described above wherein the compound of claim 1 wherein Formula I has the structure

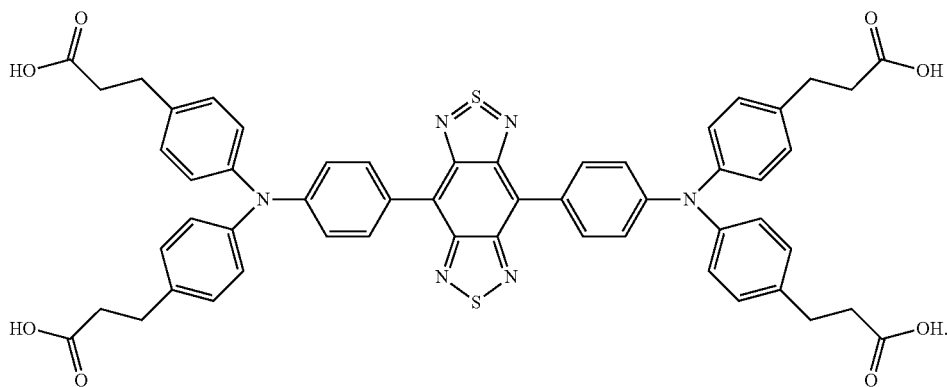 [SMILES: O=C(O)CCc1ccc(N(c2ccc(CCC(=O)O)cc2)c2ccc(-c3c4c(c(-c5ccc(N(c6ccc(CCC(=O)O)cc6)c6ccc(CCC(=O)O)cc6)cc5)c5nsnc35)N=S=N4)cc2)cc1]

In certain aspects, the invention comprises a compound wherein said hydrophilic polymer is further conjugated to a targeting ligand. In certain aspects, the invention comprises a compound as described above wherein the targeting ligand is an antibody molecule. In certain aspects, the invention comprises a compound as described above wherein the antibody molecule is an Fv fragment, a single-chain Fv, a diabody, or an affibody molecule. In certain aspects, the invention comprises a compound as described above wherein the compound having a peak fluorescent emission at about 100 nm.

In certain aspects, the invention comprises a compound as described above having Formula II:

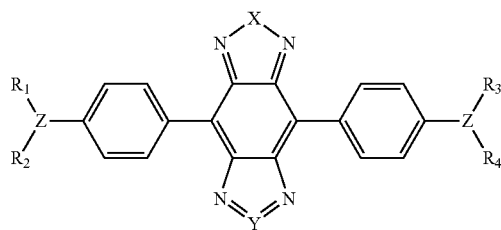

wherein X and Y are independently selected from the group consisting of S and Se;
Z is N or P; and
R1, R2, R3 and R4 are independently one of

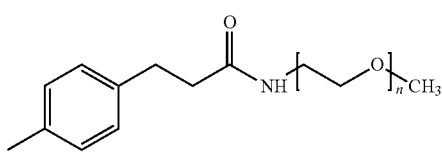
(a)

wherein n is an integer ranging from 1 to 100,

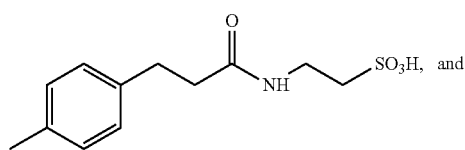
(b)

-continued

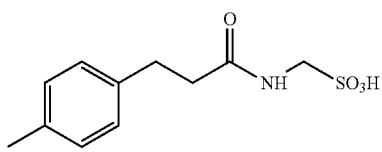
(c)

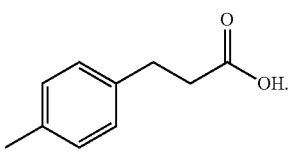
(d)

In certain aspects, the invention comprises a compound as described above wherein R1, R2, R3 and R4 are each

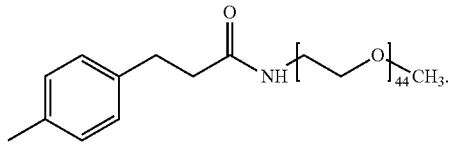

In certain aspects, the present invention comprises a method for imaging a biological structure in a tissue, said method using an NIR-II dye and comprising steps of:

(a) introducing the dye into a tissue and allowing the dye to bind to a structure within the tissue;

(b) exposing the dye, bound to the biological structure, to NIR light;

(c) detecting NIR-II light emitted from the dye as a result of the NIR light provided in step (b); and (d) constructing an image from the emitted light in step (d) using a detector sensitive to NIR-II light, wherein said dye has the structure Formula II

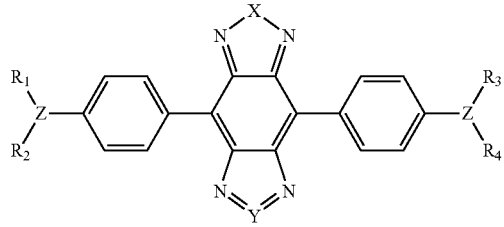

wherein
X and Y are each independently selected from S and Se;
Z is N or P; and
R1, R2, R3 and R4 are each independently of the formula "-benzyl-alkyl-linker," wherein alkyl is —(CH$_2$)$_n$— further wherein n is between 1 and 4, inclusive and "linker" is selected from the group consisting of carboxyl, hydroxyl, NH-ester, maleimide, amine, —SH, or hydrazide. In some embodiments, R1, R2, R3, and R4 have the same structure.

In certain aspects, the present invention comprise a method as described above, wherein R1 is of one of the formula (a)

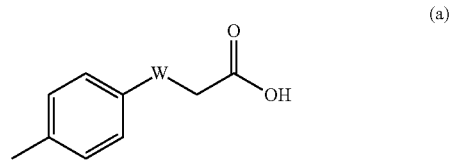

wherein W is —(CH$_2$)$_m$— where m is 1 to 10;

(b)

(c)

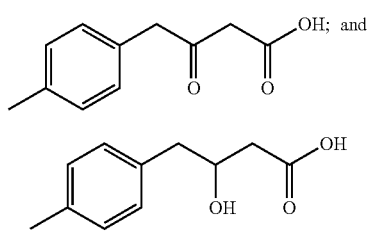

In certain aspects, the invention comprises a method as described above wherein the NIR light is provided by an excitation wavelength between 650 and 1000 nm from a laser. In certain aspects, the present invention comprises a method as described above, wherein the biological structure is within a living subject. In certain aspects, the present invention comprises a method as described above, wherein the biological structure is a tumor or a lymph node. In certain aspects, the present invention comprise a method as described above, further comprising a targeting ligand linked to one of R1, R2, R3, and R4. In certain aspects, the present invention comprises a method as described above, wherein the targeting ligand is an affibody, antibody or peptide or aptamer molecule.

In some aspects of the present invention, the compound as described above is a targeting ligand that is specific to an EGFR. In certain aspects, the present invention comprises a method as described above, wherein the biological structure is greater than 3 mm below an external surface of a subject. In certain aspects, the present invention comprises a method as described above, wherein the biological structure is in a subject being evaluated for head and neck cancer, melanoma, or breast cancer. In certain aspects, the present invention comprises a method as described above, wherein the image is constructed with an InGaAs camera. In certain aspects, the present invention comprises a method as described above, wherein constructing the image comprises using a longpass filter at wave length between 1000 and 1700 nm. In some aspects of the present method, a compound as described above is injected intravenously. In some aspects of the present method, a compound as described above is further used for image-guided tumor surgery. In some aspects of the present method, a compound as described above is used by applying photothermal heating of tissue which has taken up the compound and is thereafter irradiated at a site of interest by a near-infrared light source. In some aspects of the present method, a compound as described above is used in a method wherein the compound is excited with NIR to generate photoacoustic signals.

The present methods, using compounds of the present invention, may be used to create images as stated above, and further comprising constructing the image comprises using a longpass filter at wave length between 1000 and 1700 nm. In certain aspects of the present invention, the imaging methods comprise use of the D-A-D small molecule injected intravenously. The method may further comprise, in certain aspects, use of a D-A-D small molecule as described here for image-guided tumor surgery.

Certain aspects of the present invention comprise synthesizing a fluorescent small molecule comprising the sequential steps of: (a) synthesizing a (2E,2'E)-diethyl 3,3'-((phenylazanediyl)bis(4,1-phenylene))diacrylate; (b) synthesizing a diethyl 3,3'-((phenylazanediyl)bis(4,1-phenylene))dipropanoate; (c) synthesizing a diethyl 3,3'-(((4-bromophenyl)azanediyl)bis(4,1-phenylene))dipropanoate; (d) synthesizing a bis(2-(trimethylsilyl)ethyl)3,3'-(((4-bromophenyl)azanediyl)bis(4,1-phenylene)) dipropanoate; (e) synthesizing a bis(2-(trimethylsilyl)ethyl)3,3'-(((4-bromophenyl)azanediyl)bis(4,1-phenylene)) dipropanoate; (f) protecting the compound of step (e) and linking it to a diheteroaryl compound to form a compound having a di-substituted diheteroaryl compound having alkyl-aryl substituents from step (d); (g) Attaching a heteroaryl compound to react with the alkyl-aryl compound to add an additional fused ring; (h) deprotecting the compound of step (g) to produce a D-A-D NIR-II fluorescent small molecule having four carboxyl groups (final compound).

Certain aspects of the synthesis outlined above comprise the use of invention is the use of a TMS (trimethylsilyl) compound in the synthesis of the present dye. This compound, e.g., 2-(trimethylsilyl)ethanol) as shown e.g. in compound 8, is attached to two arms of a dye precursor (compound 5 in FIG. 2) and provides a reactive site for the attachment of a linker on all four arms of the dye.

Certain aspects of the present invention comprise different starting materials to yield different cyclic compounds shown above as circles A and B.

Certain aspects of the present invention comprise the use of the compounds as described in a method of photothermal heating of tissue which has taken up the compound and is thereafter irradiated at a site of interest by a near-infrared light source. In certain aspects of the present invention, the compounds as described may be used in a method in which the compound is excited with NIR to generate photoacoustic signals.

DETAILED DESCRIPTION OF THE PREFERRED EMBODIMENT

Definitions

Figure 1:
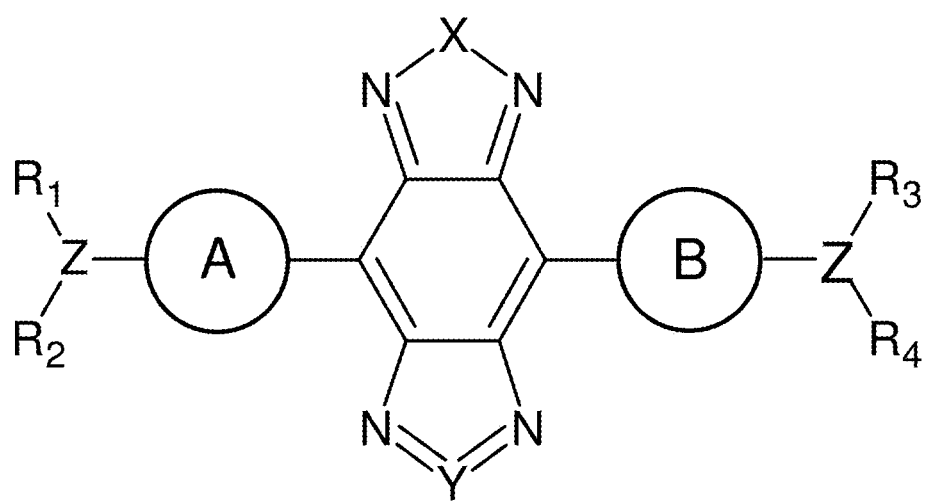
FIG. 1 is a representation of a chemical structure showing the core of an NIR-II dye according to the present invention and linking groups R1-R4 for attachment to hydrophilic polymers.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclature utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "D-A-D NIR-II fluorescent small molecule" refers to compounds having a pi-conjugated donor-acceptor-donor structure, and substituents imparting fluorescence in the NIR-II wavelength range. Such NIR-II dyes are typically in a general class of heteroquinoid dyes, as described in G. Qian et al., "Band Gap Tunable, Donor-Acceptor-Donor Charge-Transfer Heteroquinoid-Based Chromophores: Near Infrared Photoluminescence and Electroluminescence. Chem. Mater. 20, 6208-6216 (2008)," cited below. Such dyes are referred to as D-π-A-π-D (or D-A-D) type of near-infrared fluorescent compounds based on benzobis (thiadiazole) and its selenium analogues. Given the teachings herein, one of skill in the art can synthesize alternative NIR-II dyes having efficient emission at a wavelength between 1000-1700 nm.

For example, the present methods may be applied to compounds described in U.S. Pat. No. 7,842,758 B2, "Near infrared emissive fluorophores; Polymer band-gap reduction through augmentation of pi-backbone quinoidal character; (porphinato)(metal) moiety; ethynyl moiety; [1,2,5]thiadiazole or pentacenyl moiety; electronics, optics, emissive agents, treatment of disease, imaging, drug delivery; polymersomes." As described there, compounds derived from the core groups below:

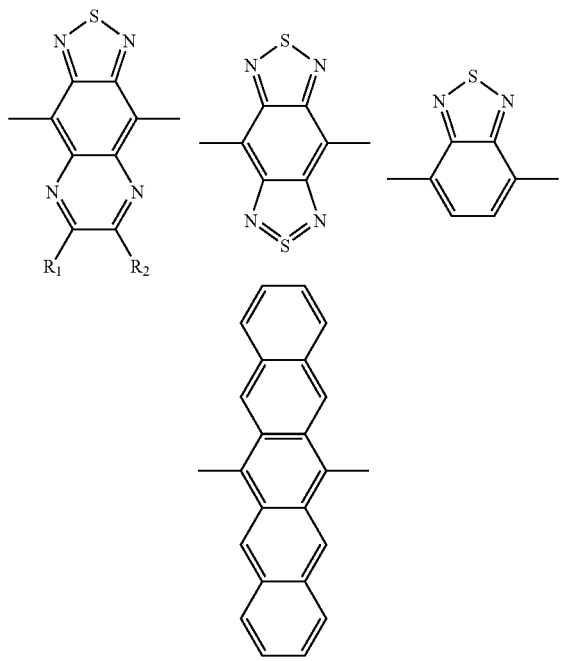

can be modified as taught here to be solubilized, and, if desired, coupled to a targeting ligand such as an affibody molecule etc. Compounds derived from core groups such as:

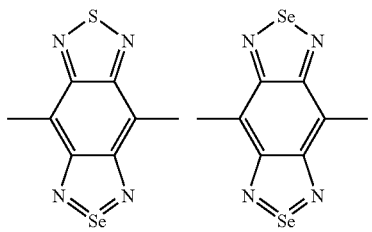

can also be modified as taught here to be solubilized, and, if desired, coupled to a targeting ligand such as an affibody molecule etc.

Another example of a benzobis(thiadiazole) compound useful in the present invention is given in U.S. Pat. No. 8,519,087, "Benzobis(thiadiazole)-based alternating copolymer and preparation thereof", disclosing compounds such as:

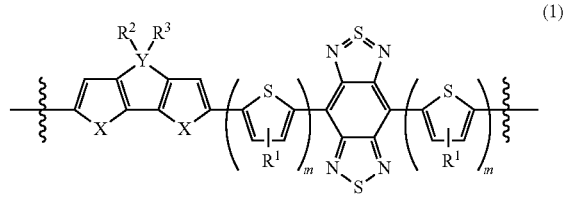

(1)

A dash "-" that is not between two letters or symbols is used to indicate a point of attachment for a substituent. For example, —CONH$_2$ is attached through the carbon atom.

The term "carboxyl" refers to the —C$_x$OOH group, where x is from 1 to 6.

The term "hydroxyl" refers to the Cx-OH group, where x is from 1 to 6.

The term "NHS-ester" refers to an N-Hydroxysuccinimide (NHS) ester, of the formula

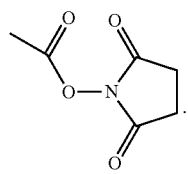

The term "maleimide" as a linker refers to the group

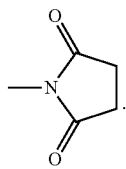

The term "amine" refers to —NH$_2$ and -alkyl-NH$_2$.

The term "hydrazide" refers to —C$_x$(=O)NH—NH$_2$ where x is from 1 to 6.

As used herein, the terms "alkyl" or "alkylene" is intended to include both branched and straight chain saturated aliphatic hydrocarbon groups having the specified number of carbon atoms. For example, "C1-14 alkyl" (or alkylene), is intended to include C1, C2, C3, C4, C5, C6, C7, C8, C9, C10, C11, C12, C13 and C14 alkyl groups. Additionally, for example, "C1-C6 alkyl" denotes alkyl having 1 to 6 carbon atoms. Alkyl groups can be unsubstituted or substituted so that one or more of its hydrogens are replaced by another chemical group. For example, alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. The term "lower alkyl" refers to an alkyl group as defined above, having 2-8 carbon atoms. The term "lower alkyl acid" refers to a lower alkyl as described above, further containing a carboxylic acid group, such as a methanoic acid, ethanoic acid, propanoic acid, butanoic acid, pentanoic acid, hexanoic acid, ethanedioic acid, 2-hydroxypropanoic acid, 2-hydroxybutanedioic acid, 2-hydroxypropane-1,2,3-tricarboxylic acid, and 2-aminoethanesulfonic acid. For example, "lower alkyl acid may be represented by —(CQ)n-COOH, where n is between 1 and 10 and Q is CH$_2$, CHOH, CNH, or CO.

The term "alkenyl" refers to an unsaturated alkyl group as described above having at least one double bond.

The term "aryl" refers to monocyclic or bicyclic aromatic hydrocarbon groups having 6 to 12 carbon atoms in the ring portion, such as phenyl, and naphthyl groups, each of which may be substituted.

The term hydrophilic compound refers to natural or synthetic polymer having a high affinity for water, being capable of taking up a large volume of water and becoming a hydrogel. A "water-soluble" polymer is a hydrophilic polymer capable of dissolving in an aqueous solution. Examples include PEG, the polysaccharides in their natural or modified forms, in the form of amides, esters, ethers, urethanes and the like; the proteins in their native or denatured forms as well as the polypeptides and their derivatives; the acrylic polymers, such as polyacrylic and methacrylic acids, their salts, esters, amides, anhydrides, nitriles and their copolymers; the polymers of the polycarboxylic acids such as fumaric, maleic, malic, succinic and citric acids, their salts, esters, amides, anhydrides, nitriles and their copolymers; polyethylene or polyoxyethylene glycol, their derivatives and copolymers; polyethylene imine, its derivatives and copolymers; polystyrene sulfonate and polystyrene phosphonate, their derivatives and copolymers; polyvinyl sulfonate and polyvinyl phosphonate, their derivatives and copolymers; vinyl polyalcohol, its derivatives and copolymers; the polyvinyl pyridines, their salts, derivatives and copolymers; polyvinyl pyrrolidone, its derivatives and copolymers; or a mixture of at least two of these.

The term "PEG" refers to polyethylene glycol, i.e. any water soluble poly(ethylene glycol) or poly(ethylene oxide). The expression PEG will comprise the structure —(CH$_2$CH$_2$O)$_n$—, where n is an integer from 2 to about 1000. A commonly used PEG is end-capped PEG, wherein one end of the PEG termini is end-capped with a relatively inactive group such as alkoxy, while the other end is a hydroxyl group that may be further modified by linker moieties. An often used capping group is meth-oxy and the corresponding end-capped PEG is often denoted mPEG. Hence, mPEG is CH$_3$O(CH$_2$CH$_2$O)$_n$—, where n is an integer from 2 to about 1000 sufficient to give the average molecular weight indicated for the whole PEG moiety, e.g., for mPEG Mw 2,000 Dalton, n is approximately 44 (a number that is subject to batch-to-batch variation). The notion PEG is often used instead of mPEG. "PEG" followed by a number (not being a subscript) indicates a PEG moiety with the approximate molecular weight equal to the number. Hence, "PEG2000" is a PEG moiety having an approximate molecular weight of 2000 Dalton. Specific PEG forms of this invention are branched, linear, forked, dumbbell PEGs, and the like and the PEG groups are typically polydisperse, possessing a low polydispersity index of less than about 1.05.

The term "small molecule" refers to any molecule, or chemical entity, with a molecular weight of less than about 5,000 Daltons.

The small molecule of interest here is an NIR fluorophore, or dye, which refers to a molecule that has an absorption resulting in emission wavelength in the NIR-II spectrum between 1000-1700 nm. NIR molecular probes work in a preferential wave range for in vivo fluorescence imaging called "biological window." These molecules can be detected deeper while minimizing the absorption of the fluorescence by tissues. As is generally understood, a fluorophore (or fluorochrome, similarly to a chromophore) is a fluorescent chemical compound that can re-emit light upon light excitation.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, the term "about" means plus or minus 5% of a stated numerical value.

The term "targeting ligand" is used in combination of an NIR-II dye as described here that is linked to a molecule or molecular fragment that specifically binds to a marker of interest in a target, e.g. in vivo. For example, targeted imaging probes for detecting cancer cells are provided that specifically bind cellular targets on cancer cells in vivo. In general, the targeting ligand's cellular targets can be proteins exposed on the surface of cancer cells and the imaging probes are able to access and bind these targets in vivo. The disclosed targeting ligands preferably do not bind normal (e.g. non-cancerous) tissue. In some embodiments, the targeting ligands, linked to the present dyes, bind to metastasized cancer cells or cells about to undergo metastasis from the primary tumor. Examples of binding to EGFR are provided here.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668). Dabs can be composed of a single variable light or heavy chain domain. In a certain embodiment of the invention, the variable light domain and/or variable heavy domain specific for MISIIR are inserted into the backbone of the above mentioned antibody constructs. Methods for recombinantly producing antibodies are well known in the art. For example, commercial vectors comprising constant genes to make IgGs from scFvs are provided by Lonza Biologics (Slough, United Kingdom). The phrase "Affibody molecule" may also refer to "Affibody® molecule." Affibody is a trademark owned by Affibody AB. Affibody is a trademark registered in Sweden, Europe, and the United States and under trademark application in Japan.

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

With respect to antibodies, the term "immunologically specific" refers to antibodies that bind to one or more epitopes of a protein or compound of interest, but which do not substantially recognize and bind other molecules in a sample containing a mixed population of antigenic biological molecules. As used herein, the term "immunotoxin" refers to chimeric molecules in which antibody molecules or fragments thereof are coupled or fused (i.e., expressed as a single polypeptide or fusion protein) to toxins or their subunits. Toxins to be conjugated or fused can be derived from various sources, such as plants, bacteria, animals, and humans or be synthetic toxins (drugs), and include, without limitation, saprin, ricin, abrin, ethidium bromide, diptheria toxin, Pseudomonas exotoxin, PE40, PE38, saporin, gelonin, RNAse, protein nucleic acids (PNAs), ribosome inactivating protein (RIP), type-1 or type-2, pokeweed antiviral protein (PAP), bryodin, momordin, and bouganin.

The term "affibody molecule" refers to a molecule that consists of three alpha helices with 58 amino acids and has a molar mass of about 6 kDa. A monoclonal antibody, for comparison, is 150 kDa, and a single-domain antibody, the smallest type of antigen-binding antibody fragment, 12-15 kDa. See, for exemplary details of affibody structures and uses, Orlova, A; Magnusson, M; Eriksson, T L; Nilsson, M; Larsson, B; Höidén-Guthenberg, I; Widström, C; Carlsson, J et al. (2006). "Tumor imaging using a picomolar affinity HER2 binding affibodymolecule", *Cancer Res.* 66 (8): 4339-48. Exemplary Affibody® Molecules are commercially available from Abcam Corp. Cambridge Mass.

The term "conjugated" refers to the joining by covalent or noncovalent means of two compounds or agents of the invention.

The term "biological structure" refers to structures involved in structural biology, that can be resolved on a microscopic level by imaging.

Overview

The present invention comprises, in certain aspects, a biocompatible, aqueous soluble and rapidly renal excreted (~90% excreted within 24 hours) NIR-II fluorophore based on a synthetic 970 Da small organic molecule (CH1055). The NIR-II fluorophore outperformed indocyanine green (ICG), a clinically approved NIR-I (~800 nm emission) dye in resolving mouse lymphatic vasculature and sentinel lymphatic mapping near a tumor. High levels of uptake of PEGylated CH1055 dye were observed in mouse brain tumors, suggesting a non-invasive deep tissue tumor imaging agent. As described above, "PEGylation" refers to attachment of the fluorophore (dye) to polyethylene glycol, a water soluble polymer. As described below, the present PEGylated dyes are aqueous soluble, biocompatible, rapidly excreted and non toxic.

The CH1055 dye also provided targeted molecular imaging of tumors in vivo when conjugated with anti-EGFR affibody molecule which targets the PEGylated dye to tissue expressing EGFR (epidermal growth factor receptor). The superior tumor-to-background signal ratio afforded precise image-guided tumor removal surgery. The present dyes may be used as imaging probes for detection or imaging ex vivo or in vivo epidermal growth factor (EGFR) expressing cells. EGFR plays important roles in cell growth, differentiation, and migration. Its positive signaling was found to cause increased proliferation, decreased apoptosis, and enhanced tumor cell motility and angiogenesis. EGFR expression is frequently found in wide spectrum of human tumors of epithelial origin, including non-small cell lung cancer (NSCLC), breast, head and neck (squamous cell carcinoma of the head and neck or "SCCHN"), in addition to gastric, colorectal, esophageal, prostate, bladder, renal, pancreatic, ovarian, and brain cancers. EGFR can thus be used as a tumor or cancer specific target for receptor-mediated delivery systems of therapeutic agents and imaging probes.

Also described is the synthesis of molecular fluorophores (e.g. CH1055, 0.97 kDa), and their use for in vivo NIR-II imaging and image-guided surgery. The PEGylated CH1055 exhibited a high aqueous solubility, a peak fluorescent emission at ~1100 nm and a molecular mass of 8.9 kDa, well within the size limit of ~40 kDa for renal excretion. Pharmacokinetics of CH1055-PEG demonstrated rapid urine excretion with ~90% removal through the renal system within 24 hours post-injection (PI), affording the first NIR-II fluorophore with excretion levels comparable to FDA approved fluorophores. The NIR-II imaging quality, on the other hand, with CH1055-PEG was far superior to that of ICG for imaging mouse blood and lymphatic vasculatures, tumors and lymph node mapping. (22) CH1055-PEG showed high passive tumor uptake, capable of non-invasively identifying tumors within a mouse brain through intact scalp and skull at a depth of ~4 mm. Molecular imaging with CH1055 conjugated to an anti-epidermal growth factor receptor (EGFR) affibody molecule was accomplished through highly specific targeting of a xenograft human squamous cell carcinoma tumors in immune-deficient mice. NIR-II imaging afforded a 5-fold higher tumor-to-normal tissue ratio than traditional NIR-I imaging, allowing accurate image guided tumor removal surgery. (23)

Significant improvements in imaging resolution and depth could be achieved by transitioning to the NIR-II window due to reduced photon scattering and autofluorescence background at longer wavelengths. The use of the NIR-II window will allow physicians to see deeper anatomical features with a much higher degree of clarity as well as enable new imaging capabilities that are not feasible with NIR-I fluorophores. In order for NIR-II fluorescence imaging to translate from small animal studies into a clinical setting, the total body clearance of the NIR-II contrast agent is critical. To date, all other NIR-II fluorophores are largely retained or show very slow excretion rates. For the first time we developed a small molecule based NIR-II fluorophore to afford rapid renal excretion. This combined with the lack of any cellular toxicity in vitro at imaging doses opens a door for clinical translation.

Also for the first time, it is shown that a NIR-II molecular fluorophore drastically out-performs an FDA approved NIR-I counterpart for imaging blood and lymphatic vasculatures in terms of image clarity, spatial resolution and depth of penetration owing to the reduced tissue scattering that follows an inverse wavelength dependence ($\sim\lambda^{-\alpha}$, $\alpha$=0.22-1.68).(11) In addition to improved resolution of both lymph nodes and vessels, CH1055-PEG's ability to accurately pinpoint tumors passively during sentinel lymph node mapping provides an added benefit to an already useful NIR-II contrast agent. After an intradermal injection of CH1055-PEG when applied to SLN mapping, the sentinel lymph nodes draining the tumor in conjunction with any previously undetected tumors can both be simultaneously visualized with high fidelity.

CH1055 is a versatile NIR-II dye capable of tumor detection through either non-specific uptake when PEGylated or molecular imaging when conjugated to a targeting ligand. CH1055-PEG shows strong tumor accumulation as demonstrated through the non-invasive imaging of brain tumors with both the skull and scalp left intact. The high degree of imaging clarity in conjunction with a high tumor-to-normal tissue ratio at a depth of ~4 mm through multiple tissues with distinct scattering coefficients reaffirms the possible benefits garnered by imaging within the second near-infrared window in a clinical setting.

Fluorescence imaging is the most suitable approach to molecular image-guided surgery owning to the high temporal and spatial resolution which allows for rapid, precise resection of tumors having unique molecular signatures. As targeted surgery is especially suitable for tumors that are difficult to differentiate from the surrounding healthy tissue such as in breast cancers, NIR-II molecular imaging agents are ideal considering the limited NIR-II tissue autofluorescence. (35) When employing the same targeting ligands for molecular imaging, the switch from NIR-I to NIR-II fluorophores imparts significant benefits in tumor detection as seen in the big boost in the tumor-to-normal tissue ratio gained by the NIR-II fluorophore.

Photoacoustic imaging (PAI) is a newly emerging technique in biomedical imaging that provides strong optical absorption contrast and high ultrasonic resolution, which could overcome the depth and resolution limits of conventional optical imaging techniques. Using near-infrared (NIR, 650-900 nm) absorptive materials as exogenous contrast agents has been widely applied because it improves PAI sensitivity and deep tissue penetration ability. With the rapid development of nanotechnology, numerous inorganic nanomaterials, such as gold, silver, and copper nanoparticles (NPs), and a few organic nanomaterials such as carbon nanotubes have been evaluated as PAI contrast agents. Our NIR-II fluorophore CH1055 and its analogues can absorb light and also transfer the energy into heat. This heat can be used for many important applications including PAI and photothermal therapy.

It is also contemplated that the present compounds may be used in combination with other imaging modalities. As described in Sampath et al., "Near infrared fluorescent optical imaging for nodal staging," J Biomed Opt. 2008 July-August; 13(4):041312, the present compounds may be used in functional lymph imaging and, further, dual-labeled agent ((111) In-DTPA)(n)-trastuzumab-(NIR-II dye) can utilize the high photon count provided by an NIR fluorescent dye for possible detection of HER2 metastasis in lymph node.

Materials and Methods Used in Examples

Optical Characterization

The NIR fluorescence spectrum was taken using a home-built NIR spectroscopy setup. The excitation source was a 200-W ozone-free mercury/xenon lamp (Oriel), which was dispersed by a monochromator (Oriel) to generate an excitation line with a bandwidth of 15 nm. The excitation light was allowed to pass through the solution sample in a 1-mm-path cuvette (Starna Cells, Inc.), and the emission was collected in a transmission geometry. The excitation light was collected in the 790-1500 nm emission range. The emitted light was directed into a spectrometer (Acton SP2300i) equipped with a liquid-nitrogen-cooled InGaAs linear array detector (Princeton OMA-V). Spectra were corrected post-collection to account for the sensitivity of the detector and extinction feature of the filter. Photostability was determined by spiking CH1055-PEG into serum, PBS, and DI and exposing it in a 1-mm path length cuvette (Starna Cells, Inc.) to continuous 808 nm excitation at a power density of 0.3 W/cm$^2$ and taking images every 10 seconds for ~1 hour. Stability was determined by measuring the ROI and comparing the fluorescence intensity to the starting fluorescence signal.

Urine Excretion

Urine was collected without coercion from 5 balb/c mice for the 24 hours after injection with CH1055-PEG. Mice were placed in plastic cages with available water and urine was collected with a 20 µL pipette. To determine excretion levels, urine was drawn up into a capillary tube and the fluorescence measured (1200 LP, ~20 ms exposure, 2D InGaAs array Princeton Instruments) along with the minimal background fluorescence in control urine and glass capillary tube.

Before solely using the fluorescence of the excreted CH1055-PEG to measure the amount of excreted dye per mouse, the fluorescence intensity of the injected dose and a series of dilutions in PBS were measured in order to check the linearity. At higher concentrations, non-linear relationships between fluorescence and concentration occur due to variety of reasons such as inter-sample quenching effects. Within the above concentration range, the relationship between fluorescence intensity and concentration was linear as demonstrated below:

To determine linearity and starting with a generalized formula:

$$y = a * x^k$$

becomes the following on a log-log plot:

$$\log(y) = \log(a) + k * \log(x)$$

The slope on a log-log plot will determine whether the function is linear or follows an exponential relationship. Selecting two points:

$$\log[F(x_1)] = m * \log(x_1) + b$$

$$\log[F(x_2)] = m * \log(x_2) + b$$

$$m = \frac{\log(F_2) - \log(F_1)}{\log(x_2) - \log(x_1)}$$

$$m = \frac{\log\left(\frac{F_2}{F_1}\right)}{\log\left(\frac{x_2}{x_1}\right)}$$

where m=k is the slope of the line on the log-log plot which corresponds to the power of the generalized equation $y = a * x^k$.

As m=1.0 from the linearity check, y=a*x and there is a linear dependence between concentration and fluorescence intensity within this concentration range.

The % ID was measured in the following way:

$$\% \ ID = \frac{\sum_{m=1}^{m=s_f}((I_m - I_{control}) * V_m)}{(I_{injected} - I_{control}) * V_{injected}}$$

where s is the number of a urine time-point from a particular mouse starting at the first urine time-point collected $s_1$ until $s_f$, the last urine time-point collected, I is the average fluorescent intensity as measured with a 1200LP filter, $I_{control}$ is the fluorescent intensity of control urine at the same exposure time as the sample $I_n$, $I_{injected}$ is the fluorescent intensity of the injected dose, and V is the volume of the urine, and $V_{injected}$ is the volume of the injected CH1055-PEG.

The agglomerate cumulative excretion profile was formulated in the following way:

The urine excretion time (t), volume (V), and fluorescence intensity (I) were gathered from all mice in the excretion study (n=5).

The excretion time (t), volume (V), and fluorescence intensity (I) from all the mice used in the study were rearranged in the following way:

$$\begin{pmatrix} t_1 & I_1 & V_1 \\ \vdots & \ddots & \vdots \\ t_f & I_f & V_f \end{pmatrix}$$

with the sample number $s_1$ at $t_1$ corresponding to the earliest urine time-point out of all the mice in the study and $s_f$ at $t_f$ corresponding to the last time-point out of all the mice in the study.

The % $ID_{total\ (n=5)}$ was calculated in the following way:

$$\% \ ID_{total(n=5)} = \frac{\sum_{m=1}^{m=s_f}((I_m - I_{control}) * V_m)}{\sum_{n=1}^{n=5}(((I_{injected} - I_{control}) * V_{injected})_n)}$$

where s is the number of a urine time-point from all the mice in the study starting at the first urine time-point collected $s_1$ until $s_f$, the last urine time-point collected, I is the average fluorescent intensity as measured with a 1200LP filter, $I_{control}$ is the fluorescent intensity of control urine at the same exposure time as the sample $I_n$, $I_{injected}$ is the fluorescent intensity of the injected dose, and V is the volume of the urine, and $V_{injected}$ is the volume of the injected CH1055-PEG, and n corresponds the number of a mouse used in the study.

The agglomerate excretion curve treats all of the individual mice as one system (or a 'super-mouse') and measures the total CH1055-PEG injected and all of the urine excreted from all of the mice.

This was deemed the easiest way to portray the urine excretion data since urine was collected without coercion and time-points vary between mice.

NIR-II Video Rate Imaging

Mice were placed on a stage with a venous catheter for injection of contrast and imaging agents. All NIR-II images were collected on a 320×256 pixel two-dimensional InGaAs array (Princeton Instruments). The excitation laser was an 808 nm laser diode at a power density of ~0.3 W/cm². Emission was typically collected with a 1200 nm LP filter. A lens set was used for obtaining tunable magnifications, ranging from 1× (whole body) to 2.5× (high magnification) magnification by changing the relative position of two NIR achromats (200 mm and 75 mm, Thorlabs). A binning of 1 and a variable exposure time was used for the InGaAs camera (320×256 pixel) to capture images in the NIR-II window. Images were processed with Matlab.

U87MG Orthotopic Brain Tumor Implantation

All aspects of experimental manipulation were in strict accord with guidelines from the National Institute of Health and have been approved by members of the Stanford Institutional Animal Care and Use Committee (IACUC). Eight week old female nude mice (Charles River) were anesthetized using 2.0% isoflurane and positioned in a Benchmark® (Leica) stereotactic instrument. The top of the mouse's head was cleaned with 70% ethanol and betadine. Ophthalmic ointment was applied. A sagittal skin incision of 0.5 cm was made over the bregma and the skull was exposed. A burrhole in the left hemisphere was drilled according to the coordinate 0.5 mm anterior and 2.0 mm lateral to the bregma. A 10 μL gas-tight syringe (Hamilton Company, Reno, Nev.) with a 26-gauge needle (Cat 800010) was inserted to the striatum and lowered to the depth of 2.5 mm from the dural surface. U87 MG-Luc cells (5 μL, $2 \times 10^4$ cells in PBS) was injected into the striatum over 15 min using a microsyringe pump controller (World Precision Instruments, Inc., Sarasota, Fla.). The same amount of PBS was also injected as an experimental control. The needle was left for 10 minutes before being withdrawn. The burrhole was occluded with glue to prevent leakage of cerebrospinal fluid, and the skin was then sutured. Animals were used for experiments after 10 days, when tumors had reached a size of approximately 2~ mm diameter as determined by MM.

Affibody-CH1055 Conjugation

For Affibody-CH1055 conjugation, CH1055: HBTU: DIPEA: 1-(2-amino-ethyl)-pyrrole-2,5-dione hydrochloride=1:1.1:20:1 was added to DMSO at room temperature and reacted 2.5 h to get the CH1055-Maleimide. The EGFR Affibody used in this study contains a unique C-terminal cysteine residue for thiol-reactive maleimide dye labeling. To reduce the spontaneously formed disulfide bond between the cysteine residues, the Affibody molecules were incubated with 5 mM TCEP.HCl. The excess TCEP.HCl was removed by passing the reaction mixture through a Zeba Spin Desalting Column (Fisher Scientific). The CH1055-Maleimide was reconstituted in DMSO to a concentration of 10 mM and added to the Affibody solution. The reaction mixture was incubated at room temperature for 3 hours. HPLC was then used for purification (C18, 5 μm, 5-95% acetonitrile/water with 0.1% TFA) to get the pure CH1055-Affibody.

Brain Tumor NIR-II Imaging

Brain tumor imaging was performed using both the high magnification and whole body NIR-II setups. NIR-II imaging was performed with a variety of filters and exposure times. For brain tumor imaging, a 1200 LP filter was employed with an exposure time ranging from 400-800 ms. For imaging in the NIR-IIa region, a 1300 LP filter was used which required a variable exposure time ranging from 1-2 seconds. Mice were imaged 3, 6, 12, 24, 48, and 72 hours PI.

EGFR+ Targeted NIR-II Imaging and Guided-Surgery

For EGFR+ targeted imaging, a 1200 LP filter was used and mice were imaged every hour up until 6 hours as well as at 24 hours.

Photoacoustic Imaging Analysis of Phantoms

For studying the PAI properties of the compound, a cuboid container was half filled with 1% agarose gel to half depth. Different concentrations of compounds aqueous solutions were filled into polyethylene capillaries and then the capillaries were laid on the surface of solidified agarose gel. The capillaries were further covered with thin 1% agarose gel to make the surface smooth. PA spectra and PA/US coregistered images were acquired with a LAZR commercial instrument (VevoLAZR; VisualSonics). It is equipped with a LZ-250 linear array transducer and a tunable Nd:YAG laser system (680-970 nm). In our system, the Vevo LAZR PAI System with a laser at excitation wavelength of 700 nm and a focal depth of 10 mm was used to acquire PA and US images. The laser at excited wavelength ranging from 680 nm to 970 nm was sequentially enhanced with a step of 3 nm for the scan of PA spectra. Acquisition rate of 5 frames per second was used for all the experiments. The photoacoustic gain was kept at 42 dB, dynamic range at 18 dB and center frequency of 21 MHz for all studies. US and PA images were obtained sequentially. The PA signals reported were the average pixel intensities from within the Regions of Interest (ROIs). Normalization and quantification of the images were carried out using ImageJ.

Photothermal Heating of CH1055-PEG In Vitro

To study the photothermal effect of CH1055-PEG induced by NIR irradiation in vitro, 50 μL of CH1055-PEG was irradiated as well as the same volume of control PBS with a 808 nm NIR laser and 0.6 Wcm$^{-2}$ irradiation power for 150 sec. Thermal images and temperatures of solutions were recorded at every 10 seconds by a MikroShot thermal camera (Mikron).

Cytotoxicity of CH1055-PEG

We determined the CH1055-PEG toxicity in vitro with a MTS assay using a CellTiter96 kit (Promega) on U87MG cells. Approximately 5,000 cells were incubated per well with 100 μL of EMEM growth medium and serially diluted CH1055-PEG solution (n=6 for each concentration). The cells were kept at 37° C. in a humidified atmosphere containing 5% $CO_2$ for 36 hours in the presence of CH1055-PEG at different concentrations. Immediately before addition of 15 μL of CellTiter96, a colorimetric indicator of cell viability, the CH1055-PEG-spiked medium was removed from each well plate and replaced with fresh medium. After 1 h, the color change was quantified using a plate reader and taking absorbance readings at 490 nm. Cell viability was plotted as a fraction of the absorbance of control wells incubated without CH1055-PEG. Doxil was used as the negative control. The concentration was measured as a factor of the hindlimb injection concentration.

General Synthesis Information

All air and moisture sensitive reactions were carried out in flame-dried glassware under a nitrogen atmosphere. Reactive liquid compounds were measured and transferred by gas-tight syringes and were added in the reaction flask through rubber septa. Tetrahydrofuran (THF) was freshly distilled from sodium benzophenoneketyl. Dichloromethane, toluene and DMF were distilled from $CaH_2$. Sulfo-SMCC (Sulfosuccinimidyl 4-[N-maleimidomethyl]cyclohexane-1-carboxylate) was purchased from Thermo Scientific (Rockford, Ill.). $PEG_{2000}$-$NH_2$. All other standard synthesis reagents were purchased from Sigma-Aldrich Chemical Co. (St. Louis, Mo.) and used without further purification. The cell line was obtained from the American Type Tissue Culture Collection (Manassas, Va.). Female athymic nude mice (nu/nu) were purchased from Charles River Laboratories (Boston, Mass.). 4,4'-(Phenylazanediyl) dibenzaldehyde(1), 4,7-dibromo-5,6-dinitrobenzo[c][1,2,5]thiadiazole(7), Affibody molecule Ac-Cys-$Z_{EGFR.1907}$: (Ac-CVDNKFNKEMWAAWEEIRNLPNLNGWQMTA-FIASLVDDPSQSANLLAEAKKLNDAQA PK-NH$_2$) (SEQ ID NO: 1) were prepared according to literature methods (Wang et al., *Macromolecules* 44, 8771-8779 (2011); Uno et al., *Chem. Pharm. Bull.* 28, 1909-1912 (1980); Cheng et al., *Mol. Imaging Biol.* 12, 316-324 (2010)).

Analytical thin layer chromatography was performed on glass-backed silica gel plates with $F_{254}$ indicator. Compounds were visualized under UV lamp or by developing in iodine, vanillin, phosphomolybdic acid solution or with a potassium permanganate solution followed by heating on a hot plate to approximately 350° C. Flash chromatography was performed on 230-400 mesh silica gel with technical grade solvents which were distilled prior to use. $^1$H NMR spectra were recorded on a Bruker AV400 at 400 MHz as CDCl$_3$ solutions with tetramethylsilane ($\delta$=0 ppm) as the internal standard. $^{13}$C spectra were obtained on the same instruments at 100 MHz with CDCl$_3$ ($\delta$=77 ppm) as the internal reference. Chemical shifts are reported in parts per million (ppm). Multiplicities are reported as s (singlet), d (doublet), t (triplet), q (quartet), m (multiplet), dd (doublet of doublet), etc. High-resolution mass spectra were performed on Bruker APEX III 7.0 Tesla IonSpec 4.7 Tesla FTMS and Thermo Scientific LTQ ORBITRAP XL. Matrix assisted laser desorption/ionization time of flight mass spectrometry (MALDI-TOF-MS) was done by the Stanford Protein and Nucleic Acid Biotechnology Facility, Stanford University. Analytical or preparative high performance liquid chromatography (HPLC) was performed on a DIONEX ultimate 3000 instrument with PDA detection (column: Princeton-SPHER-300 C$_{18}$ 5μ, 250 mm×4.6 mm or 10.0 mm; mobile phase: water/acetonitrile with 0.1% TFA).

EXAMPLES

Example 1

Synthesis of C111055, C111055-PEG, C111055-4 Taurine and C111055-3 Taurine

Figure 2:
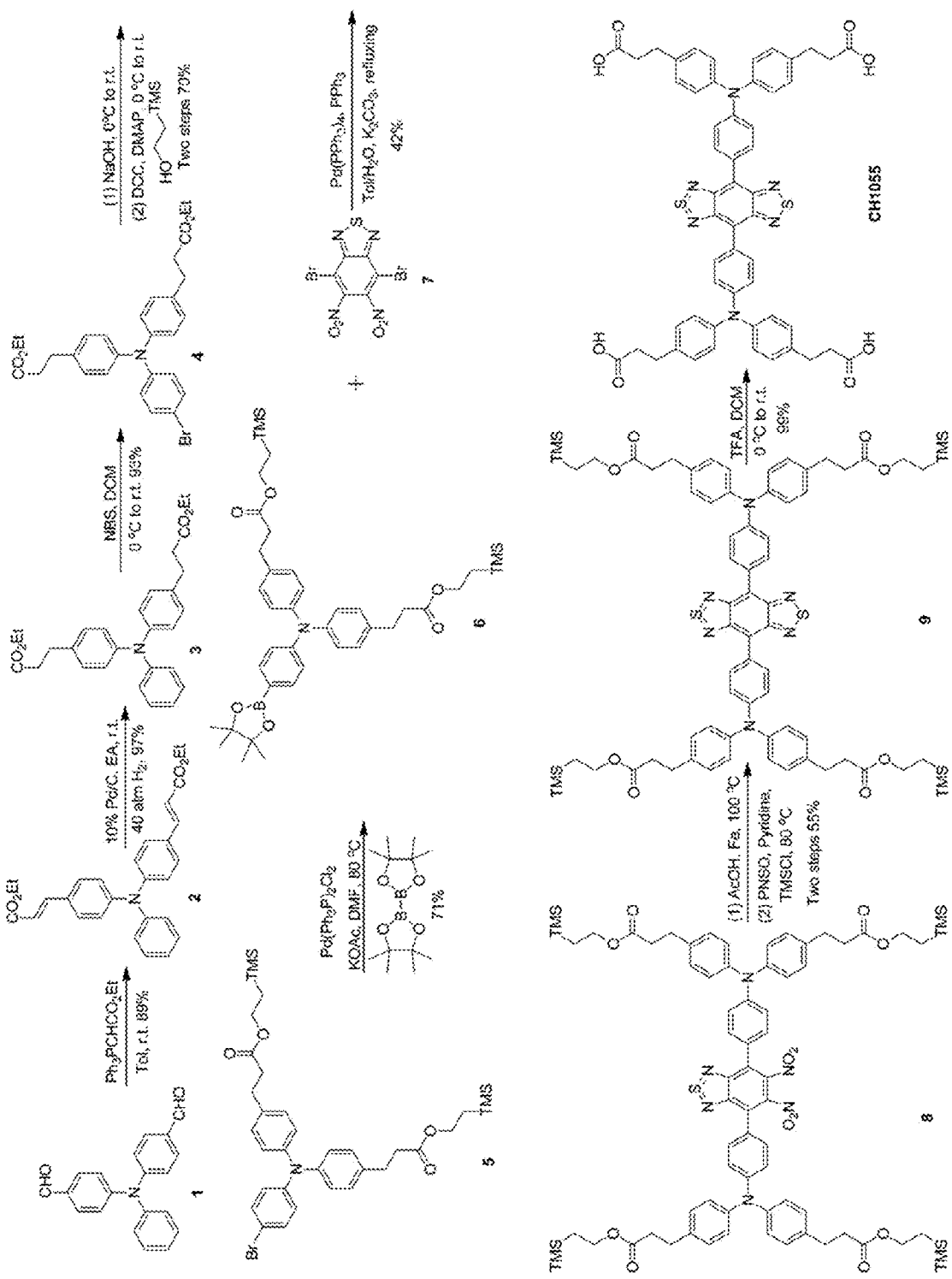
FIG. 2 is a reaction scheme showing an overview of the synthesis of CH1055.

Synthesis of a small-molecule organic NIR-II dye (CH1055, MW 0.97 kDa, FIG. 3A) was achieved with high yield from 4,4'-(phenylazanediyl)dibenzaldehyde. Key steps utilized to assemble the core structure of the target included a cross-Suzuki coupling reaction, iron reduction and N-thionylaniline induced ring closure.(24) Four carboxylic acid groups were introduced into a donor-acceptor-donor (D-A-D) type fluorescent compound to impart a certain aqueous solubility and to allow facile conjugation to targeting ligands. An overview of the synthesis of CH1055 is shown in FIG. 2. The steps in the synthesis of CH1055 were as follows:

1. Synthesis of (2E,2'E)-diethyl 3,3'-((phenylazanediyl)bis(4,1-phenylene))diacrylate(2)

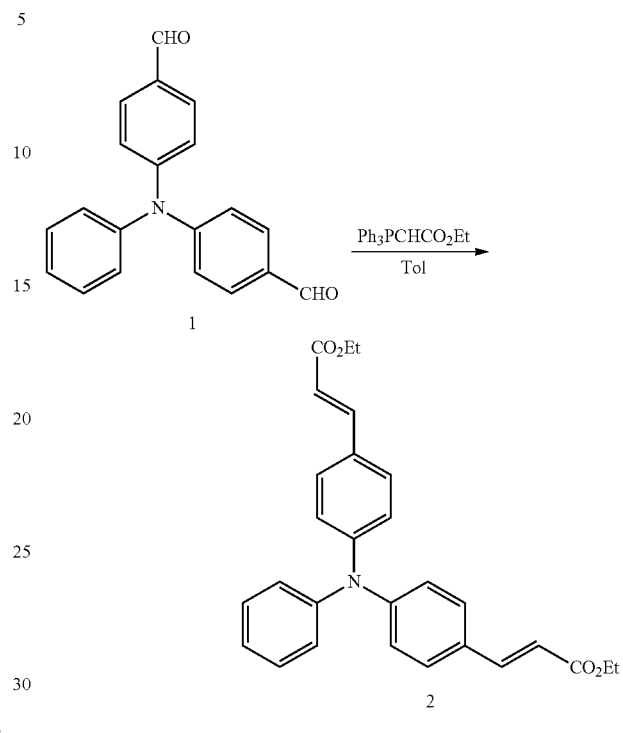

Ethyl (triphenylphosphoranylidene)acetate (26.13 g, 75 mmol) was added to a solution of aldehyde 1 (10.27 g, 34.1 mmol) in anhydrous toluene (100 mL) under an inert atmosphere (N$_2$). The solution was stirred for 48 hours at room temperature. The reaction mixture was concentrated in vacuo and the residue was purified by silica gel chromatography(petroleum ether:EtOAc=16:1 v/v) to give a bright yellow oil 2 (13.4 g, 89% yield). $^1$H NMR (400 MHz, CDCl$_3$) δ 7.64 (d, J=16.0 Hz, 2H), 7.41 (d, J=8.6 Hz, 4H), 7.32 (t, J=7.8 Hz, 2H), 7.15 (t, J=7.7 Hz, 3H), 7.07 (d, J=8.5 Hz, 4H), 6.34 (d, J=15.9 Hz, 1H), 4.27 (q, J=7.1 Hz, 4H), 1.34 (t, J=7.1 Hz, 6H). $^{13}$C NMR (101 MHz, CDCl$_3$) δ 167.2, 148.9, 146.4, 143.9, 129.73, 129.3, 128.9, 126.0, 124.8, 123.3, 116.4, 60.4, 14.4.HRMS (ESI) Calcd for: C$_{28}$H$_{28}$NO$_4^+$ ([M+H]$^+$): 442.2013. Found: 442.2000.

2. Synthesis of diethyl 3,3'-((phenylazanediyl)bis(4,1-phenylene))dipropanoate (3)

-continued

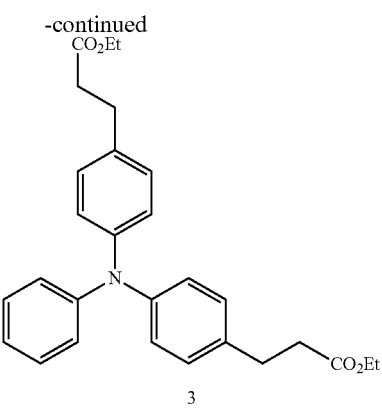

3

A mixture of 2 (6.462 g, 14.6 mmol) and 10% Pd/C (0.64 g) in EtOAc (100 mL) was evacuated and back-filled with $H_2$ (40 atm). After stirring 24 hours at room temperature, the mixture was filtered over a pad of Celite (EtOAc eluent) and the solvent was evaporated in vacuo. The crude product was further purified by silica gel chromatography (petroleum ether: EtOAc=16:1 v/v) to afford a colorless oil 3 (6.28 g, 97% yield). $^1$H NMR (400 MHz, CDCl$_3$) δ 7.09 (t, J=7.8 Hz, 2H), 7.00-6.80 (m, 11H), 4.03 (q, J=7.1 Hz, 4H), 2.80 (t, J=7.8 Hz, 4H), 2.50 (t, J=7.8 Hz, 4H), 1.14 (t, J=7.1 Hz, 6H). $^{13}$C NMR (101 MHz, CDCl$_3$) δ 173.0, 148.0, 146.1, 134.9, 129.1, 129.1, 124.3, 123.6, 122.3, 60.4, 36.0, 30.4, 14.3. HRMS (ESI) Calcd for: $C_{28}H_{32}NO_4^+$ ([M+H]$^+$): 446.2326. Found: 446.2325.

3. Synthesis of diethyl 3,3'(((4-bromophenyl)azanediyl)bis(4,1-phenylene))dipropanoate (4)

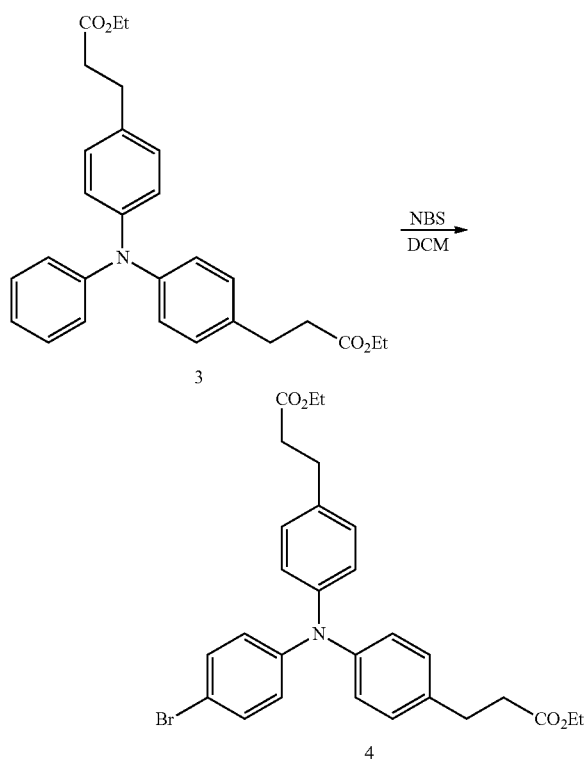

To 150 mL of DCM in a 500 mL round bottomed flask was added compound 3 (5.28 g, 11.9 mmol). After stirring at 0-5° C. for 5 min, NBS (2.25 g, 12.61 mmol) was added in 5 portions. The reaction mixture was warmed to room temperature and stirred for additional 16 hours. The reaction was then completed and filtered through a pad of Celite and concentrated in vacuo, to give a brown oil. Purification of the crude product by flash chromatography (petroleum ether: EtOAc=16:1 v/v) afforded a colorless oil 4 (5.8 g, 93% yield). $^1$H NMR (400 MHz, CDCl$_3$) δ 7.25 (d, J=8.7 Hz, 2H), 7.06 (d, J=8.3 Hz, 4H), 6.96 (d, J=8.4 Hz, 4H), 6.87 (d, J=8.8 Hz, 2H), 4.13 (q, J=7.1 Hz, 4H), 2.89 (t, J=7.7 Hz, 4H), 2.60 (t, J=7.8 Hz, 4H), 1.23 (t, J=7.1 Hz, 6H). $^{13}$C NMR (101 MHz, CDCl$_3$) δ 173.0, 147.1, 145.5, 135.5, 132.0, 129.2, 124.5, 124.5, 114.3, 60.4, 35.9, 30.4, 14.2. HRMS (ESI) Calcd for: $C_{28}H_{31}BrNO_4^+$ ([M+H]$^+$): 524.1431. Found: 524.1404.

4. Synthesis of bis(2-(trimethylsilyl)ethyl)3,3'-(((4-bromophenyl)azanediyl)bis(4,1-phenylene)) dipropanoate (5)

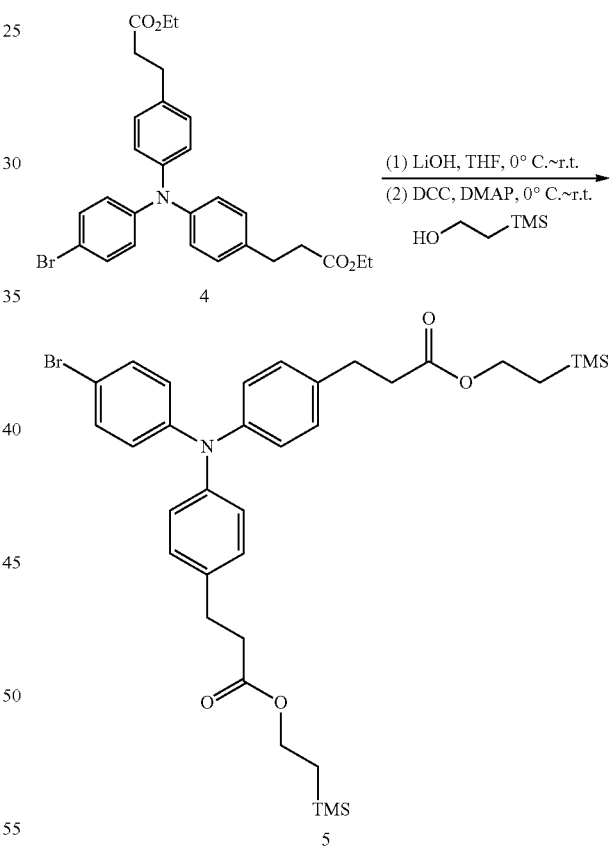

To 250 mL round bottomed flask was charged with compound 4 (4.271 g, 8.143 mmol), THF (120 mL), and the resulting solution was chilled to 0-5° C. in an ice bath. A solution of LiOH (0.9772 g, 40.715 mmol) in $H_2O$ (40 mL) was added and the reaction mixture was stirred at 0-5° C. for 1 hour and then warmed to ambient temperature. The reaction was monitored by TLC analysis and it was completed in 24 hours monitor. The reaction mixture was acidified to pH 3 with sat. aq.KHSO$_4$ solution, extracted with EtOAc (3×100 mL). The combined organic extracts were dried over anhydrous MgSO$_4$ and concentrated in vacuo. The crude product was used for the next step without further purification.

To a solution of the acid in CH$_2$Cl$_2$ (80 mL) was added 4-dimethylaminopyridine (199 mg, 1.63 mmol), N,N-dicyclohexylcarbodiimide (4.2 g, 20.36 mmol) and 2-(trimethylsilyl)ethanol (2.41 g, 20.36 mmol). The reaction was stirred at room temperature for 24 hours. The crude material was filtered through a medium porosity frit and volatiles were removed under reduced pressure. Purification of the crude product by silica gel chromatography (petroleum ether:EtOAc=32:1 v/v) afforded a colorless oil 5 (3.81 g, 70% yield). $^1$H NMR (400 MHz, CDCl$_3$) δ 7.26 (d, J=8.8 Hz, 2H), 7.08 (d, J=8.4 Hz, 4H), 6.97 (d, J=8.4 Hz, 4H), 6.89 (d, J=8.8 Hz, 2H), 4.24-4.16 (m, 4H), 2.91 (t, J=7.7 Hz, 4H), 2.60 (t, J=7.8 Hz, 4H), 1.04-0.97 (m, 4H), 0.06 (s, 18H). $^{13}$C NMR (101 MHz, CDCl$_3$) δ 172.9, 147.1, 145.5, 135.6, 132.0, 129.3, 124.5, 114.2, 62.6, 36.0, 30.4, 17.3, −1.4. HRMS (ESI) Calcd for: C$_{34}$H$_{47}$BrNO$_4$Si$_2{}^+$ ([M+H]$^+$): 668.2222. Found: 668.2232.

5. Synthesis of Compound 6

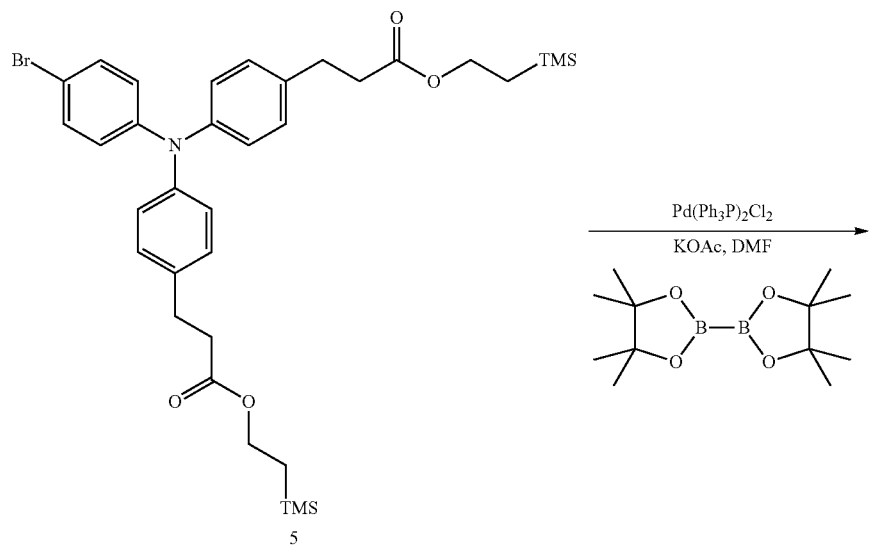

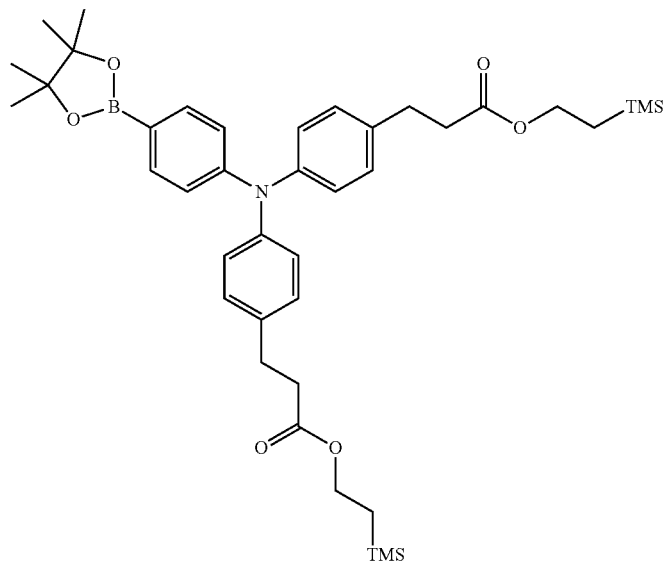

To a solution of bis(triphenylphosphine)palladium(II) dichloride(129 mg, 0.175 mmol), KOAc (413 mg, 4.21 mmol), and bis(pinacolate)diboron (535 mg, 2.11 mmol) in DMF (20 mL) was added compound 5 (1.173 g, 1.754 mmol) under an inert atmosphere (Ar). The reaction mixture was heated in an oil bath at 80° C. for 12 hours. The solution was cooled, diluted with H$_2$O (40 mL) and extracted with EtOAc (3×50 mL). The combined organic layers were washed with water (2×20 mL), dried over anhydrous MgSO$_4$ and evaporated in vacuo. The residue was purified by column chromatography (petroleum ether:EtOAc=8:1 v/v) to give compound 6 (892 mg, 71% yield) as a colorless oil. $^1$H NMR (400 MHz, CDCl$_3$) δ 7.66 (d, J=8.5 Hz, 2H), 7.11 (d, J=8.5 Hz, 4H), 7.05-6.99 (m, 6H), 4.23-4.17 (m, 4H), 2.93 (t, J=7.8 Hz, 4H), 2.62 (t, J=7.8 Hz, 4H), 1.35 (s, 12H), 1.03-0.98 (m, 4H), 0.07 (s, 18H). $^{13}$C NMR (101 MHz, CDCl$_3$) δ 173.1, 150.7, 145.5, 135.8, 135.7, 129.2, 125.1, 121.2, 83.5, 62.7, 36.1, 30.4, 24.9, 17.3, −1.4. HRMS (ESI) Calcd for: C$_{40}$H$_{59}$BNO$_6$Si$_2^-$ ([M+H]$^+$): 716.3968. Found: 716.3941.

6. Synthesis of Compound 8

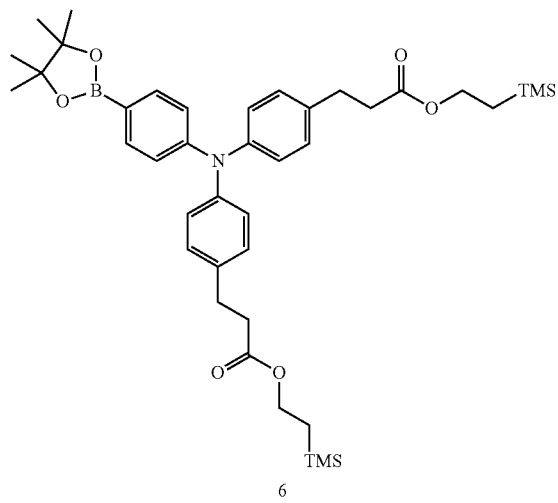

6

+

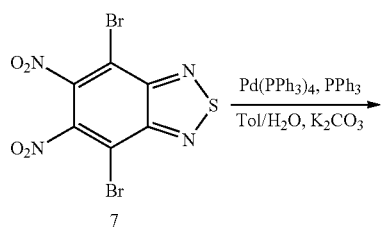

7

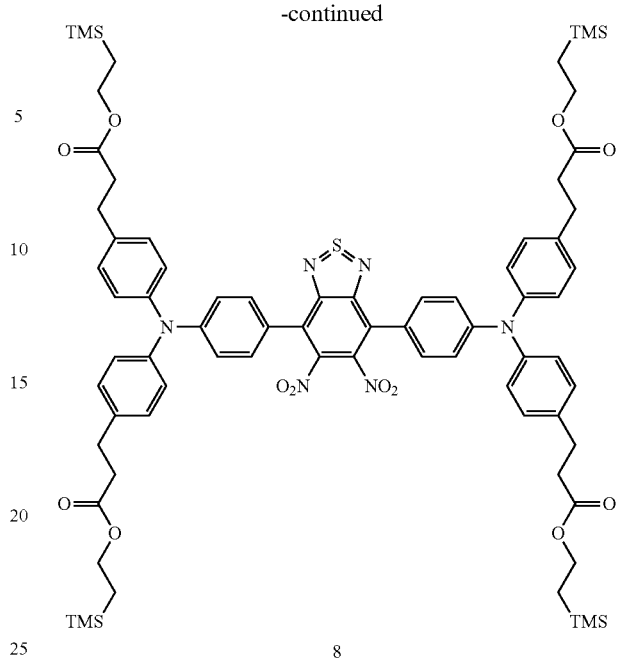

8

A 50 mL three-necked flask was charged with compound 6 (1.124 g, 1.57 mmol), compound 7 (250 mg, 0.654 mmol), and Pd(PPh$_3$)$_4$ (75 mg, 0.065 mmol), aqueous K$_2$CO$_3$ (1 M, 5 mL) in toluene (20 mL) under an inert atmosphere (Ar). The resulting mixture was further degassed with an Ar stream for 20 min and heated in an oil bath at 115-120° C. for 48 hours. The reaction was allowed to cool to room temperature and extracted with EtOAc (2×20 mL). The combined organic layers were washed with water (50 mL) and sat. brine (100 mL). After drying over anhydrous Mg$_2$SO$_4$ and removal of the solvents under reduced pressure, the residue was purified by column chromatography on silica gel (petroleum ether:EtOAc=8:1 v/v) to yield the product as a red semi-solid (385 mg, 42% yield). $^1$H NMR (400 MHz, CDCl$_3$) δ 7.47-7.38 (m, 4H), 7.20-7.07 (m, 20H), 4.24-4.18 (m, 8H), 2.96 (t, J=7.8 Hz, 8H), 2.64 (t, J=7.8 Hz, 8H), 1.04-0.98 (m, 8H), 0.06 (d, J=2.4 Hz, 36H). $^{13}$C NMR (101 MHz, CDCl$_3$) δ 173.1, 153.2, 149.9, 144.7, 142.2, 136.9, 130.2, 129.5, 127.8, 126.1, 121.8, 120.0, 62.7, 36.0, 30.4, 17.3, −1.4. HRMS (ESI) Calcd for: C$_{74}$H$_{93}$N$_6$O$_{12}$SSi$_4^+$ ([M+H]$^+$): 1401.5644. Found: 1401.5621.

7. Synthesis of Compound 9

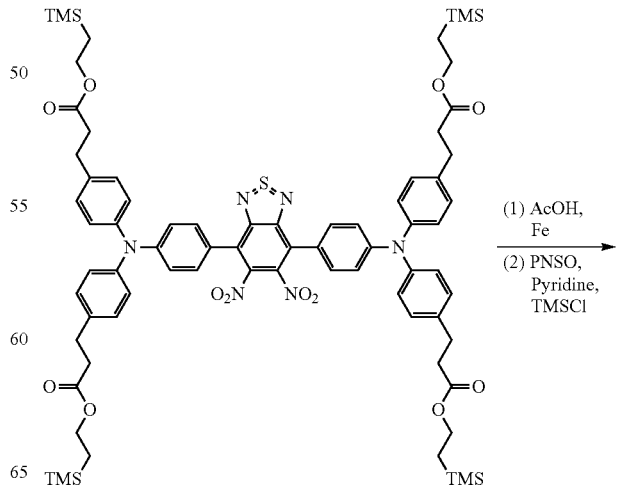

8

8. Synthesis of Compound CH1055

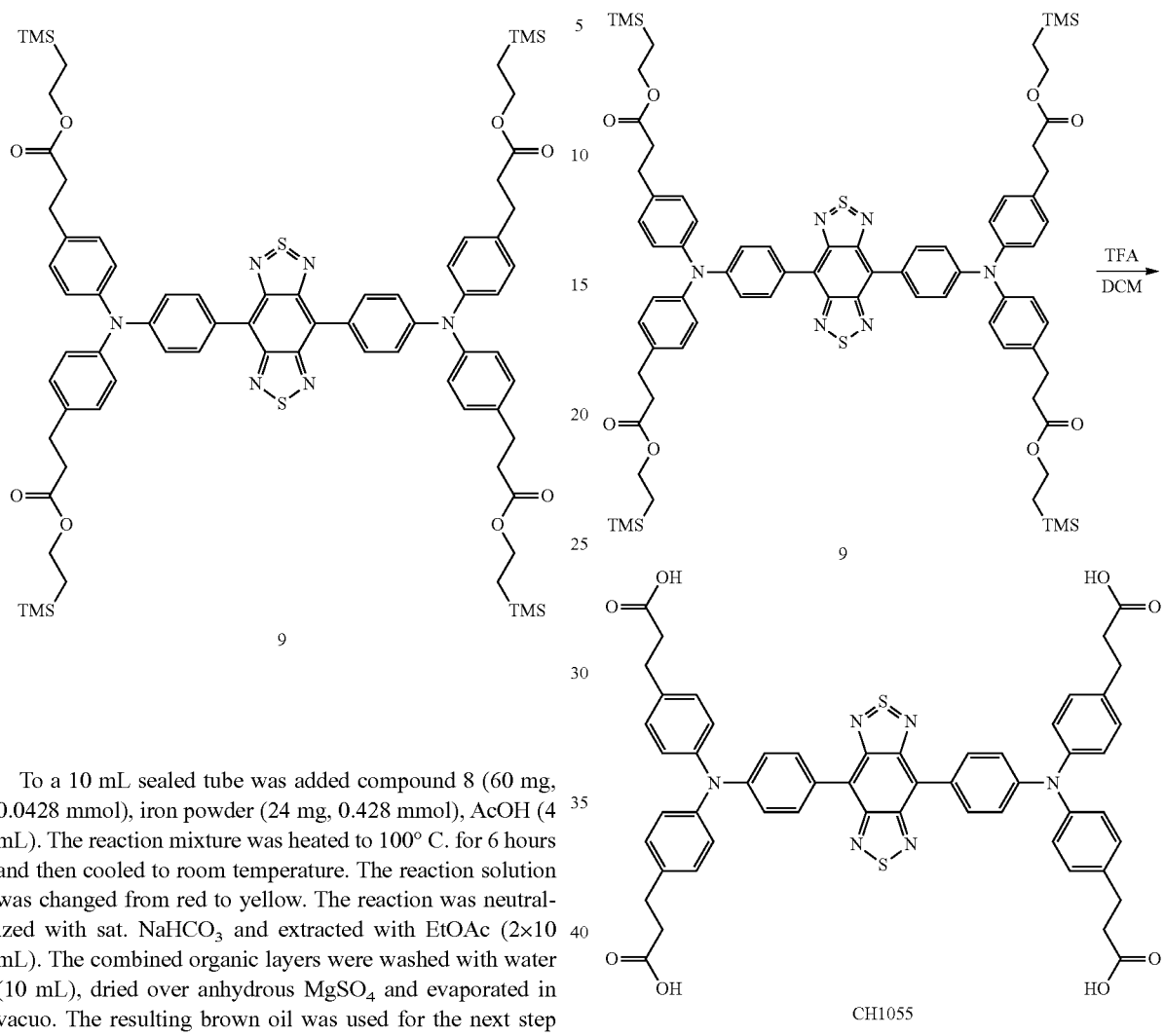

To a 10 mL sealed tube was added compound 8 (60 mg, 0.0428 mmol), iron powder (24 mg, 0.428 mmol), AcOH (4 mL). The reaction mixture was heated to 100° C. for 6 hours and then cooled to room temperature. The reaction solution was changed from red to yellow. The reaction was neutralized with sat. $NaHCO_3$ and extracted with EtOAc (2×10 mL). The combined organic layers were washed with water (10 mL), dried over anhydrous $MgSO_4$ and evaporated in vacuo. The resulting brown oil was used for the next step without further purification.

To a brownish solution in anhydrous pyridine (4 mL) was added N-thionylaniline (12.5 mg, 0.09 mmol) and TMSCl (46.5 mg, 0.428 mol). The solution was heated in an oil bath at 80° C. for 16 hours. The reaction was allowed to cool, poured into iced water, extracted with EtOAc (2×10 mL). The combined organic layers were washed with water (10 mL), dried over anhydrous $MgSO_4$ and evaporated in vacuo. The residue was purified by column chromatography on silica gel (petroleum ether:EtOAc=16:1 v/v) to yield the product 9 as a green semi-solid (32 mg, 55% yield). $^1$H NMR (400 MHz, $CDCl_3$) δ 8.19 (d, J=8.8 Hz, 4H), 7.25 (d, J=8.8 Hz, 4H), 7.22-7.13 (m, 16H), 4.26-4.18 (m, 8H), 2.96 (t, J=7.8 Hz, 8H), 2.65 (t, J=7.8 Hz, 8H), 1.05-0.99 (m, 8H), 0.07 (s, 36H). $^{13}$C NMR (101 MHz, $CDCl_3$) δ 173.0, 152.7, 148.4, 145.3, 136.1, 132.6, 129.3, 128.0, 125.6, 121.0, 120.1, 62.7, 36.1, 30.4, 17.3, −1.5. HRMS (ESI) Calcd for: $C_{74}H_{93}N_6O_8S_2Si_4^+$ ($[M+H]^+$): 1369.5568. Found: 1369.5284.

To a solution of compound 9 (10 mg, 0.0073 mg) in DCM (1 mL) was added TFA (1 mL) 0° C. The reaction mixture was slowly warmed to ambient temperature. The reaction was completed in 30 min by TLC analysis. The solvent was removed in vacuo and the crude product was washed by acetonitrile (5×5 mL) to yield the desired product CH1055 as a green semi-solid (7 mg, 99%). $^1$H NMR (400 MHz, DMSO) δ 8.10 (d, J=7.9 Hz, 4H), 7.24 (d, J=7.6 Hz, 8H), 7.08 (d, J=7.8 Hz, 12H), 2.83 (t, J=7.1 Hz, 8H), 2.56 (t, J=7.4 Hz, 8H). $^{13}$C NMR (101 MHz, DMSO) δ 174.2, 152.4, 148.2, 145.1, 136.9, 133.4, 130.0, 128.4, 125.4, 120.8, 119.5, 35.6, 30.2. HRMS (ESI) Calcd for: $C_{54}H_{45}N_6O_8S_2^+$ ($[M+H]^+$): 969.2735. Found: 969.2734.

Figure 3A:
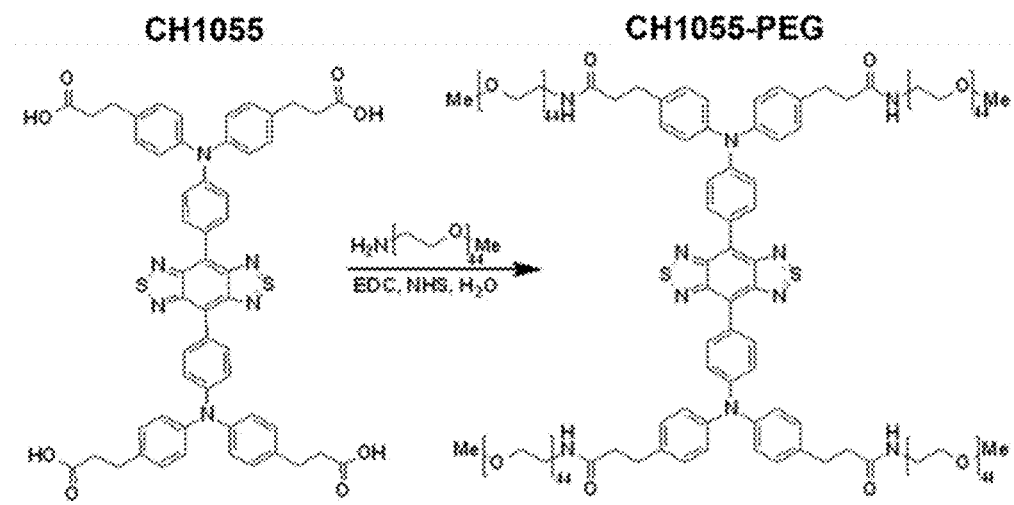
FIG. 3A, 3B is a set of figures showing synthesis of a CH1055-PEG dye (3A), and a graph showing properties of the dye (3B).
Figure 3B:
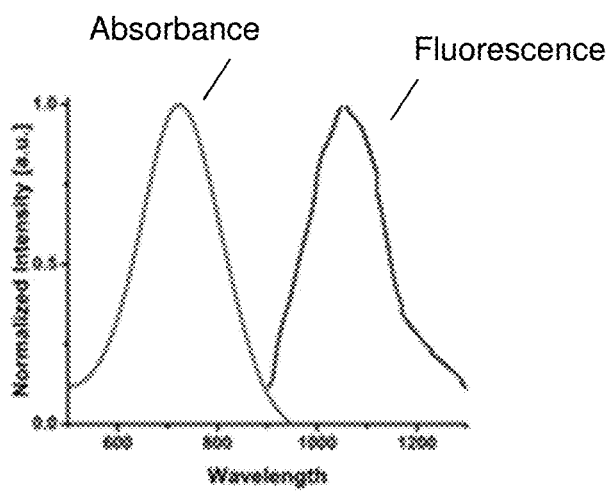
Figure 3C:
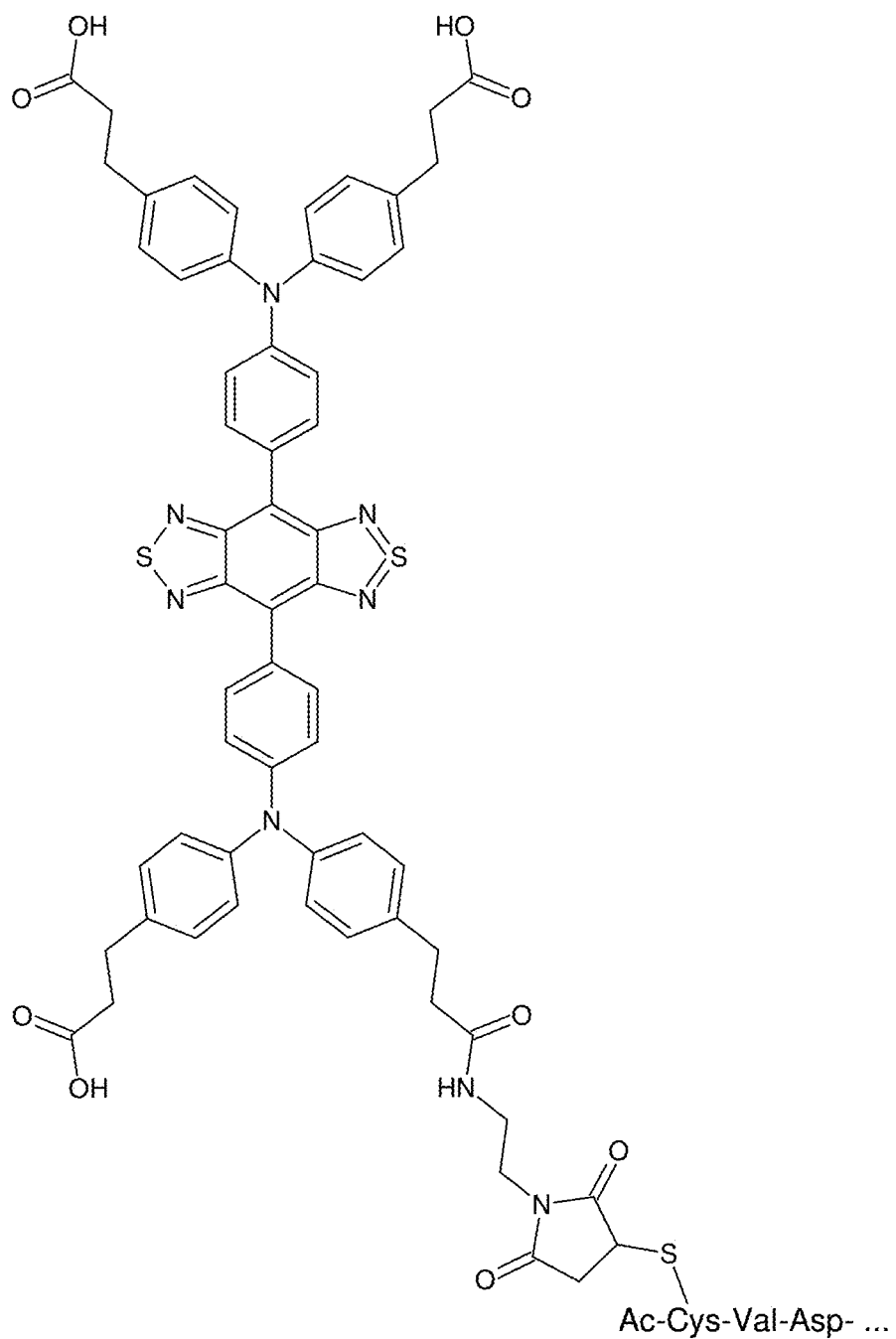
FIG. 3C is a representation of a chemical structure of an Affibody-CH1055 conjugate. Affibody molecule AC-Cys-$Z_{EGFR:1907}$ is shown linked via the sulfur atom of the cysteine residue to the rest of the structure. Only the first three amino acids of the Affibody molecule (SEQ ID NO: 1) are shown.
Figures 4A, 4B, 4C, 4D:
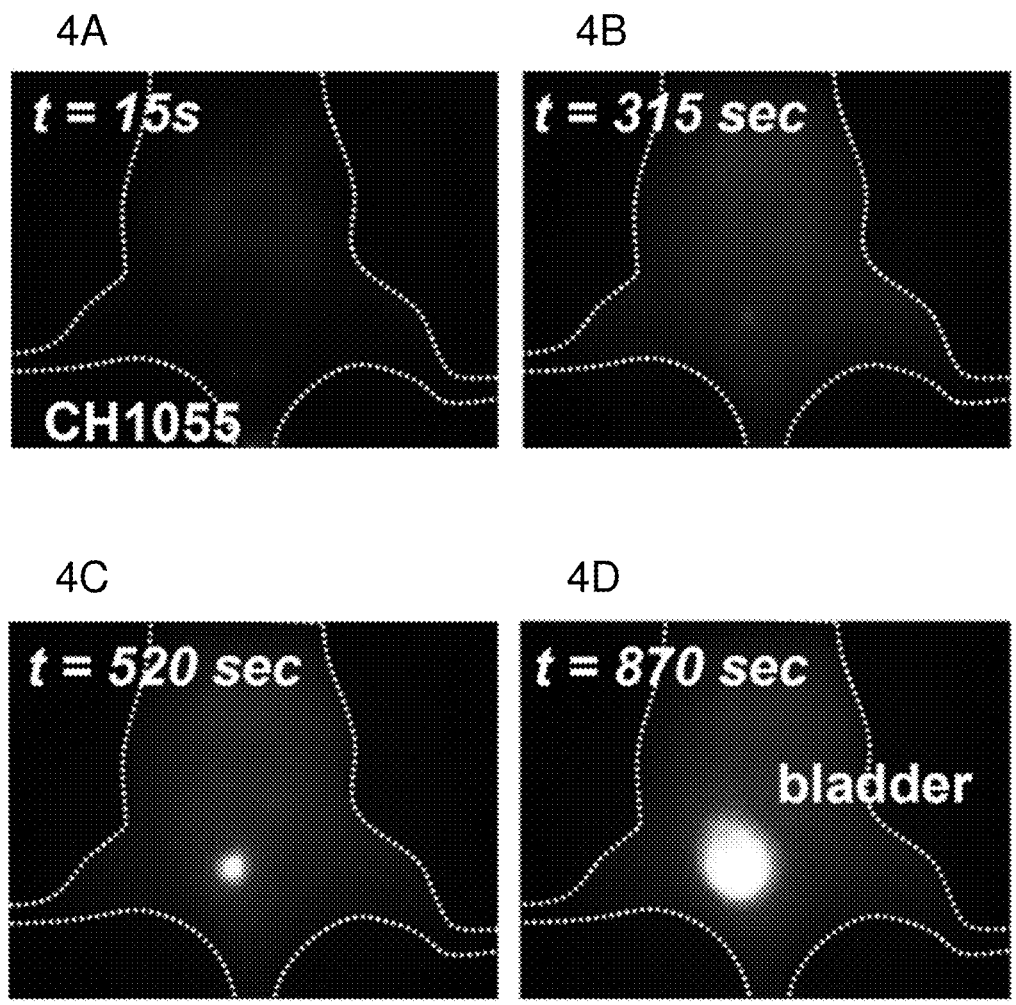
FIG. 4A, 4B, 4C, 4D is a set of figures showing series of images at time 15 seconds (4A), 315 seconds (4B), 530 seconds (4C), and 870 seconds (4D) showing bladder fluorescent signals at selected time points in a mouse injected with CH1055-PEG.

In order to further increase solubility, the carboxylic acid groups of CH1055 were PEGylated with 2 kDa PEG-$NH_2$ through EDC/NHS chemistry. FIG. 3A shows the chemical structure of CH1055 and the one-step synthesis of CH1055-PEG. A fluorescent emission spectrum was taken with an 808 nm excitation laser and demonstrated a peak emission wavelength at 1055 nm which aligned well the photoluminescence excitation mapping (data not shown). CH1055-PEG was found to be extremely photostable and the quantum yield was determined to be 0.3% by utilizing IR-26 as a reference (with a nominal QY=0.5%, data not shown).(25) The quantum yield of CH1055-PEG was on par with the majority of NIR-II nanomaterials including carbon nanotubes and thus very suitable for in vivo imaging.(9, 10, 26)

For another water soluble modification, taurine (2-aminoethanesulfonic acid) was conjugated to the CH1055 to obtain CH1055-4Taurine.

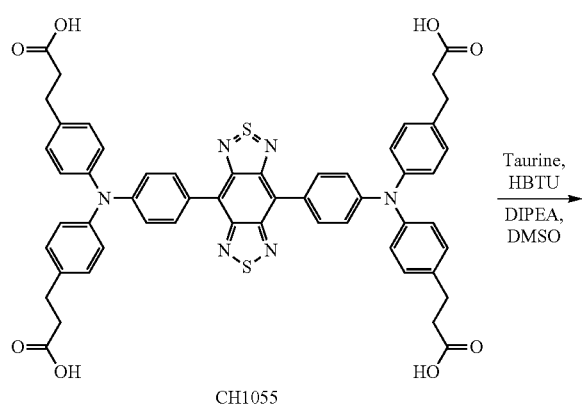

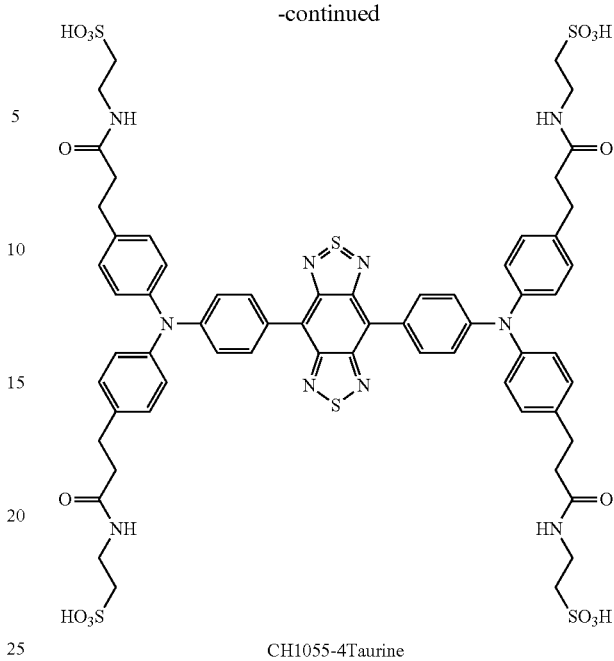

CH1055-4Taurine

To a solution of CH1055 (1 mg, 1.032 µmol) in DMF, taurine (0.774 mg, 6.192 µmol), DIPEA (18 µL), and HBTU (2.6 mg, 6.8 µmol) were added. It was stirred overnight at room temperature. HPLC purification was used to get the final product CH1055-4Taurine. HRMS (ESI) Calcd for: $C_{62}H_{65}N_{10}O_{16}S_6^+$ ([M+H]$^+$): 1397.2899. Found: 1397.2715.

Alternatively, taurine could be conjugated to the CH1055 to obtain CH1055-3 Taurine.

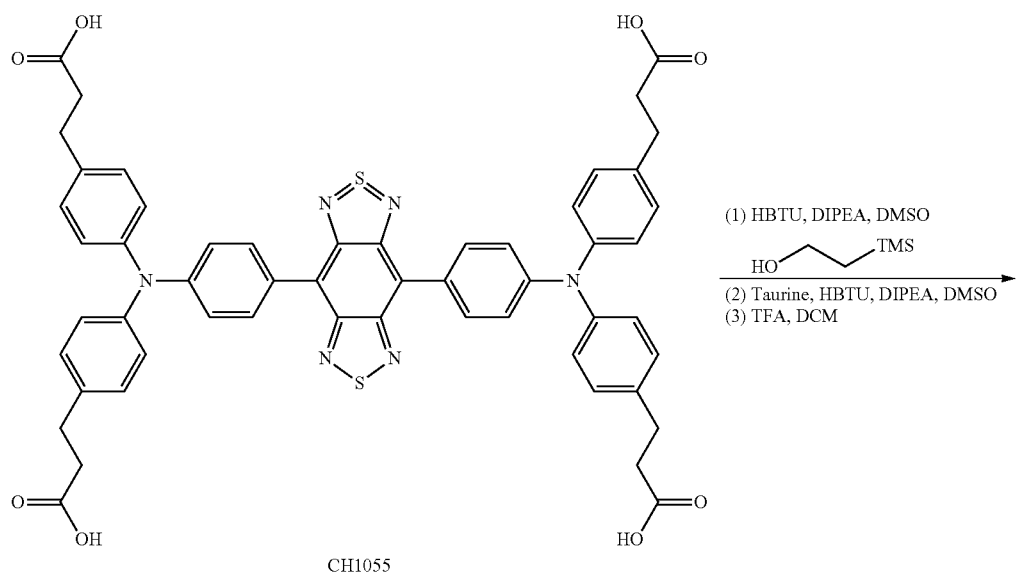

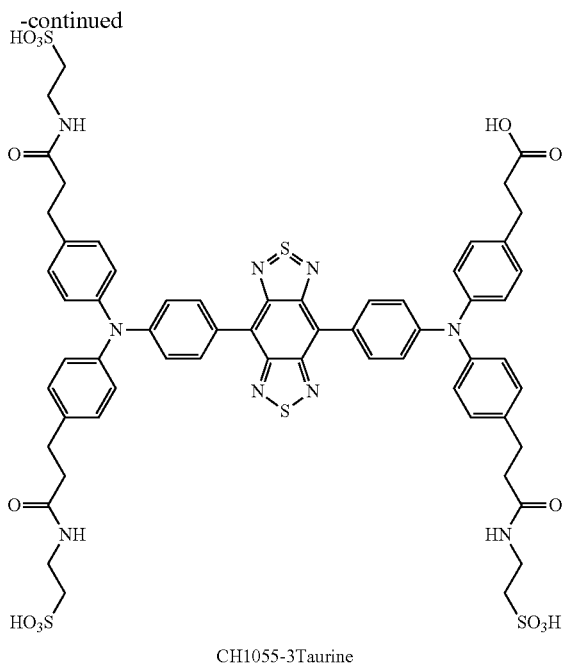

CH1055-3Taurine

To a solution of CH1055 (1 mg, 1.032 µmol) in DMF, 2-(Trimethylsilyl)ethanol (0.122 mg, 1.032 µmol), DIPEA (3.6 µL), and HBTU (0.7828 mg, 2.064 µmol) were added. It was stirred at room temperature for 24 h. Then taurine (0.774 mg, 6.192 µmol), DIPEA (18 µL), HBTU (2.6 mg, 6.8 µmol) were added. It was stirred overnight at room temperature. Then excess TFA was added. It was stirred at 0° C. for 4 h. Lastly, HPLC purification was used to get the final product CH1055-3Taurine. HRMS (ESI) Calcd for: $C_{60}H_{60}N_9O_{14}S_5^+$ ([M+H]$^+$): 1290.2858. Found: 1290.2815.

The protected modifiable side chain donor synthesis. For the donor parts, suitable commercial available triphenylamine, N,N-diphenyl-4-(thiophen-2-yl)aniline, N,N-diphenyl-thiophen-2-amine derivatives were chosen as the starting material. Then the corresponding protected side chain and were introduced. And the donor was made into borate or tributyltin compounds for the further coupling reaction. In certain aspects, R1, R2, R3 and R4 are each 3-phenylpropanoic acid or a 3-phenyl lower alkyl acid. This part comprises the sequential steps of: (a) synthesizing a (2E, 2'E)-diethyl 3,3'-((phenylazanediyl)bis(4,1-phenylene))diacrylate (compound 2); (b) synthesizing a diethyl 3,3'-((phenylazanediyl)bis(4,1-phenylene))dipropanoate (compound 3); (c) synthesizing a diethyl 3,3'-(((4-bromophenyl) azanediyl)bis(4,1-phenylene))dipropanoate (compound 4); (d) synthesizing a bis(2-(trimethylsilyl)ethyl)3,3'-(((4-bromophenyl)azanediyl)bis(4,1-phenylene)) dipropanoate (compound 5); (e) synthesizing a bis(2-(trimethylsilypethyl)3,3'-(((4-bromophenyl)azanediyl)bis(4,1-phenylene)) dipropanoate (compound 6);

Donor acceptor coupling reactions. The donors were add into the two side of the benzo[1,2-c:4,5-c']bis([1,2,5]thiadiazole) (BBTD) acceptor. Borate donors were added to the two side of BBTD by Suzuki coupling reaction. Tributyltin donors were added by Stille coupling reaction. In certain aspects, wherein R1, R2, R3 and R4 are each 3-phenylpropanoic acid or a 3-phenyl lower alkyl acid. This part comprise the sequential steps of: (f) protecting the compound of step (e) and linking it to a diheteroaryl compound to form a compound having a di-substituted diheteroaryl compound having alkyl-aryl substituents from step (d) (compound 8); (g) Attaching a heteroaryl compound to react with the alkyl-aryl compound to add an additional fused ring (compound 9).

De-protection of the D-A-D dye's side chain were performed by acid, base, hydrogenation reduction. In certain aspects, wherein R1, R2, R3 and R4 are each 3-phenylpropanoic acid or a 3-phenyl lower alkyl acid. This part comprise the sequential steps of: (h) TFA deprotecting.

The compounds above can be varied as described above, by the use of different phenyl, thiophene and benzyl-thiophne rings represented by "A" and "B" in formula I. also, the alkyl-linker can be varied to accommodate different solubilizing compounds, affibodies, etc. the linker groups, located on the distal end of the linker, can be acid groups other than the carboxyl (—COOH) group shown above. For example, these may be sulfonic (—S(O$_2$)OH, phosphonic (—P(O) (OH)$_2$, etc.

Example 2

In Vivo Biodistribution and Long-Term Fate of NIR-II Agents

Upon intravenous injection of 100 µg of CH1055-PEG in an immunodeficient nude mouse in the supine position, NIR-II video rate imaging was performed. Within a few minutes, very strong fluorescent signal was observed within the bladder and little fluorescence emanated from the liver (FIG. 4A-4D).(5, 10, 19). Background subtracted fluorescent signal intensity of both the liver and bladder regions for CH1055-PEG produced a fluorescence signal that increased significantly with time in the bladder and remained minimal in the liver up to at least 800 seconds after injection. FIG. 4A-4D shows selected time-points from video-rate NIR-II imaging (1200 nm long-pass filter, 100 ms) of a mouse in the supine position after an intravenous injection of CH1055-PEG showing disparate liver and bladder fluorescent signals.

For comparison, 200 μL of water solubilized HiPCO single-walled carbon nanotubes (CNTs) were injected (OD~10 at 808 nm) to glean the difference in in vivo biodistribution and long-term fate of NIR-II agents. Background subtracted fluorescent signal intensity of both the liver and bladder regions for CH1055-PEG (shown in FIG. 4A-4D) and HiPCO SWCNTs were created. The liver and spleen were clearly visualized almost immediately after the injection of HiPCO SWCNTs and no bladder fluorescence was noted with the SWCNT injection, but it was time-dependently found in the bladder with the CH1055-PEG, with little to no fluorescence in the liver.

Example 3

Excretion Kinetics and Assay of Toxicity

The excretion kinetics was investigated by intravenously injecting 5 balb/c mice with 100 μg of CH1055-PEG and collecting urine, feces, and blood over the course of 24 hours. With a molecular weight of 8.9 kDa and a hydrodynamic radius of ~3 nm, well below the renal filtration threshold of ~30-50 kDa, ~90% of the imaging agent was excreted through the urine within the first 24 hours post-injection (PI). (27) A CH1055-PEG agglomerated cumulative urine excretion curve for 5 mice (% ID) as well as blood circulation (% ID/g) time-points fit with an exponential decay were obtained during the 24 hours post-injection. It was shown that urine excretion of the material increased over time, and blood circulation decreased proportionately. Excretion profiles from the 5 individual mice used in the excretion study were studied over the course of 24 hours. The collected urine was visibly green due to CH1055 (data not shown). From the urine excretion data we estimated a renal elimination rate constant of 0.182 $hr^{-1}$.

Figure 5:
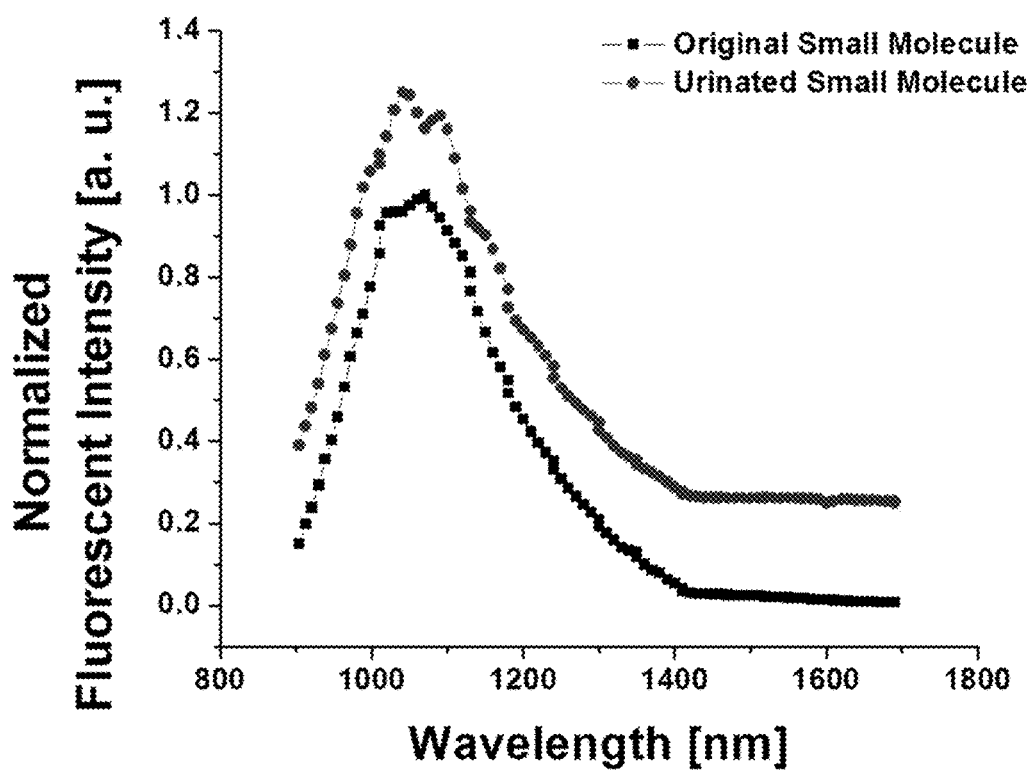
FIG. 5 is a data plot showing a fluorescence spectrum of CH1055-PEG excreted in urine.

As shown in FIG. 5, a spectral analysis of CH1055-PEG in the urine indicated no signs of metabolism in vivo. After collecting the urine excreted from a mouse, the CH1055-PEG was washed extensively to remove any small inorganic and organic compounds such as urea and dissolved ions with a 10K centrifuge filter. A fluorescence spectrum of the excreted CH1055-PEG was obtained by exciting the sample with an 808 nm excitation laser and collecting the emission with an InGaAs 1D spectrometer. No noticeable shift in the emission peak was noted, indicating that metabolism or degradation of the rapidly excreted CH1055-PEG is unlikely. However, residual low levels of CH1055-PEG that remain for longer periods of time in vivo may be metabolized and further investigation is necessary. The half-life of CH1055-PEG in blood circulation was found to be approximately 1 hour (Data not shown).

Furthermore, a preliminary cellular toxicity assay showed no observable toxicity of CH1055-PEG even at relatively high doses up to 1.5 mM (data not shown).

Example 4

Detection of Lymph Nodes, Lymphatic Vasculature and Tumor

An emerging fluorescent imaging application of ICG currently undergoing clinical trials is in detecting sentinel lymph nodes (SLN) for surgical resection.(28-30) Selectively removing sentinel lymph nodes alleviates lymphedema and other ailments that would be caused by total lymph node removal performed to prevent cancer metastasis. Fluorescent imaging has many benefits compared to the more traditional detection means that include injecting a colored dye, a radioisotope, or a combination of both. ICG is typically injected near a tumor to visualize the lymphatic vessels draining the tumor as well as the sentinel lymph nodes. To demonstrate CH1055-PEG's feasibility for SLN imaging as well as the advantages garnered by NIR-II fluorophores, a ~10 μL intradermal injection of CH1055-PEG (300 μM) and ICG (100 μM) was performed near the base of the tail of immunodeficient nude mice with shoulder xenograft U87MG tumors, followed by fluorescence imaging of the internodal collecting lymphatic vasculature and the inguinal lymph node. Immediately after injection, CH1055-PEG drainage into the internodal collecting lymphatic vasculature and the inguinal lymph node became apparent. Cross-sectional intensity profiles of the collecting lymphatic vasculature showed much sharper lymphatic features for a vessel afforded by CH1055-PEG than by ICG, owing to both reduced photon scattering and feature size broadening in the NIR-II window. A sharp intensity peak was found at a position around 6 mm with the CH1055-Peg, while the ICG showed less change in intensity with position, having a lesser intensity peak at about 10 mm. (data not shown)

Interestingly, after intradermal injections of CH1055-PEG used to image lymphatic vasculature and lymph nodes, strong tumor fluorescence was observed starting from ~5-7 hours PI, with an increasing tumor-to-normal tissue (T/NT) ratio to ~5 over the course of 24 hours. The gradual increase in fluorescence emanating from the tumor occurred while all lymphatic vessels and nodes were still visible. A day later the tumor and sentinel lymph node remained readily resolvable with little signals discernable in the liver. In contrast, intradermal injection of ICG gave obvious liver signal almost immediately post injection. While lymphatic vessels and lymph nodes were highlighted by ICG fluorescence, little tumor signal was observed. These results were consistent with hepatic clearance of ICG and little ICG tumor uptake as reported in the literature.(31)

Example 5

Non-Invasive NIR-II Fluorescence Imaging of a Glioblastoma Brain Tumor

Figure 6:
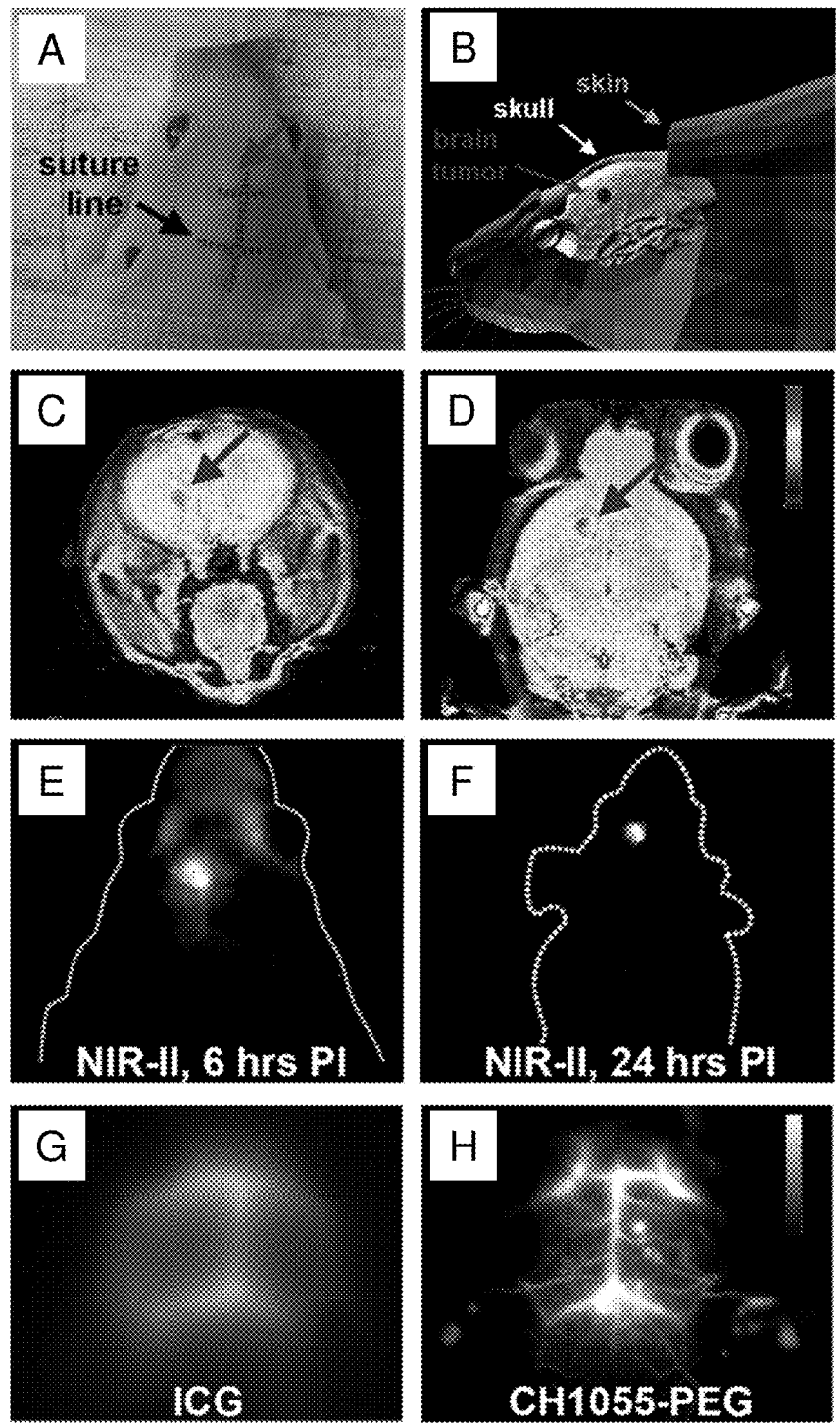
FIG. 6 is a set of images (panels A, C, D, E, F, G and H) and a schematic illustration (panel B) showing imaging of a brain tumor with CH1055-PEG.

With intravenously injected CH1055-PEG, non-invasive NIR-II fluorescence imaging of a glioblastoma brain tumor was performed through intact scalp and skull of mice. U87MG cells were surgically implanted in the mouse brain at a depth of ~4 mm within the left hemisphere (FIG. 6: panel A, panel B) and monitored with MRI to confirm the tumor's depth and size (FIG. 6: panel C, panel D). Once the tumors reached a diameter of ~2-3 mm, CH1055-PEG (100 μg) was injected intravenously and NIR-II fluorescence from the tumor derived from passive uptake reached a tumor-to-normal tissue ratio of 3.2 (1200LP, 400 ms) 6 hours PI during high-magnification NIR-II imaging (FIG. 6 panel E). After 24 hours, the tumor was clearly visible with a T/NT of ~4 when using a whole body imaging setup (FIG. 6 panel F). Within 72 hours, a T/NT of 5.5 was ultimately reached (1300LP, 1 s), surpassing the Rose criterion which states that an SBR of 5 is needed to distinguish image features with 100% certainty.(8) The tumor-to-normal tissue ratio for brain tumor imaging with CH1055-PEG was quantified with a variety of magnifications and filters, namely 1×, 1300 LP, 2.5×, 1300LP, 1×1200 LP, and 2.5×1200 LP (data not shown). While lower exposure times are needed when utilizing a 1200 nm long-pass filter, the use of a 1300 nm long-pass filter provides a quantifiable improvement in imaging quality. Above, the 1× (magnification for the whole body set-up) shows a higher T/NT ratio than the 2.5× (magnification for the brain, hindlimb set-up) due to the lower magnification. Furthermore, it was not possible to achieve a signal-to-background ratio (SBR) above a ratio of 5 which would meet the Rose criterion, when utilizing a 1200 LP filter. An SBR above 5 was only achievable with a 1300 nm long-pass filter. The results suggested CH1055-PEG as an excellent NIR-II tumor imaging agent through intradermal or intravenous injection.

Example 6

In Vivo NIR-II Fluorescence Imaging of Brain and Hindlimb Vasculature

To clearly demonstrate the advantages garnered by imaging at longer wavelengths, the brain vasculature in C57BL/6 mice with both the skin and the scalp left intact was performed with ICG (FIG. 6 panel G) as well as CH1055-PEG (FIG. 6 panel H). A drastic difference in imaging quality was observed, indicating that both brain tumors and brain vasculature can be visualized with a much higher degree of clarity in the NIR-II/IIa region than traditional NIR imaging. In further experiments, in vivo NIR-II vascular fluorescence images with CH1055-PEG and ICG were prepared. Hindlimb vascular imaging was carried out with ICG and CH1055-PEG to compare imaging quality with NIR-I and NIR-II fluorescence imaging. Fluorescent cross-sectional profiles were prepared for both ICG and CH1055-PEG taken perpendicular to the femoral artery (data not shown). Brain vascular imaging was carried out with ICG and CH1055-PEG. Representative fluorescent cross-sectional profiles for both ICG and CH1055-PEG taken perpendicular to the superior sagittal sinus showed distinct peaks of intensity at certain positions (about 11 and 16 mm), while the ICG fluorescence intensity showed similar intensity regardless of position (data not shown). ICG was imaged between 850-900 nm with a 75 ms exposure time and CH1055-PEG was imaged with a 1200 LP filter and a 200 ms exposure time for the hindlimb and a 1300 LP filter and 1 s exposure time for the brain to allow imaging in the NIR-IIa region (1300-1400 nm).

While the resolution of fine vascular features in the brain was also performed with a 1200 LP filter at an exposure time of 200 ms, a representative image of NIR-IIa imaging is shown yet a longer exposure time is required. Since CH1055's emission peak is at 1055 nm, fluorescence imaging at exposure times of <100 ms is possible with a 1000 nm filter. While utilizing a 1000 LP filter is still within the NIR-II window, the imaging quality significantly increases at progressively longer wavelengths yet slightly, yet still reasonable, exposure times are required. Intensity cross-sectional profiles clearly demonstrate the advantages of NIR-II imaging as small vessels clearly appear when utilizing CH1055-PEG, yet no fine features can be resolved with ICG other than the main femoral vessels and the superior sagittal sinus. Interestingly, the cross-sectional profile for the hindlimb, when utilizing CH1055-PEG, displays two peaks corresponding to the artery and the vein, both of which can be clearly resolved in the image.

Example 7

Specific In Vivo Tumor Targeting Using CH1055 Linked to an Anti-EGFR Affibody

Head and neck cancers are biologically similar cancers found in the oral cavity, pharynx, larynx, lips, and paranasal sinuses and account for 3% of all cancers in the United States.(32) If diagnosed early, chances for survival increase tremendously. Typically located within a centimeter from the surface of the skin, 90% of these cancers overexpress EGFR.(32) Attaching a small protein anti-EGFR affibody (~7 kDa) to NIR-II fluorophores allows for inexpensive and rapid detection of early stage head and neck cancers as well aiding physicians during tumor excision as margins will be clearly visualized. While PEGylation of CH1055 yields a rapidly excreted, versatile contrast agent capable of passive tumor uptake after both intravenous and intradermal injections, CH1055 could afford more tumor-specific targeting by linking to a molecular imaging ligand such as a 7 kDa anti-EGFR affibody. The affibody was linked to the carboxyl arms of the CH1055 using maleimidechemistry, TSTU (2-succinimido-1,1,3,3-tetramethyluronium tetrafluoroborate) and DIPEA (diisopropylethylamine) using a thiolated terminus on the affibody. First CH1055 was reacted with N-(2-Aminoethyl)maleimide to get the maleimide modified CH1055. Then the thiol of the cysteine end affibody react with the CH1055-maleimide to form the CH1055-Affibody probe.

Figure 7:
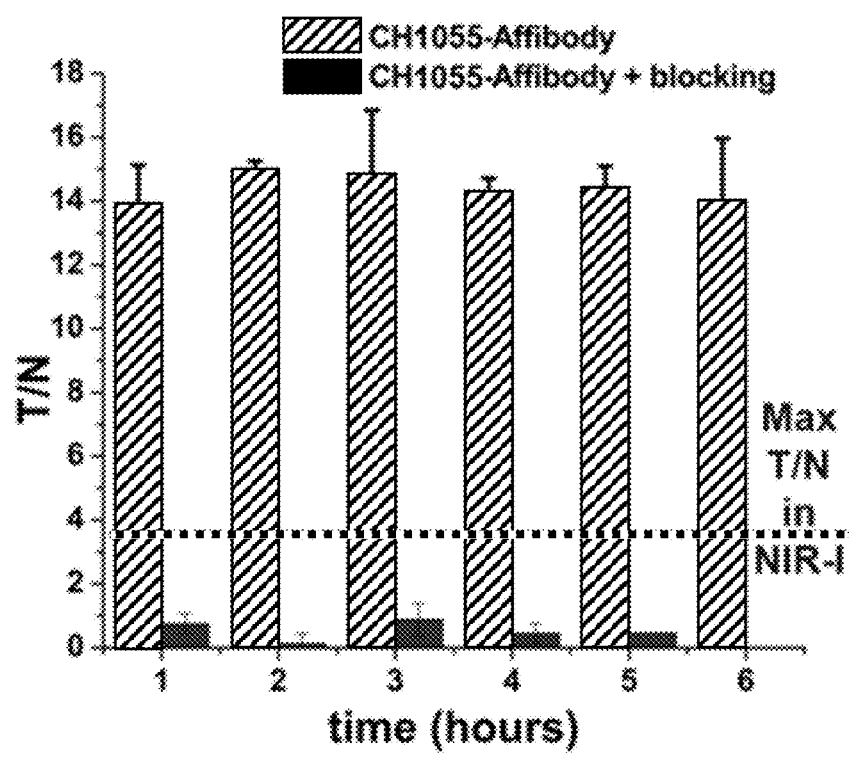
FIG. 7 is a bar graph showing results of molecular imaging of a tumor with CH1055-anti-EGFR affibody molecule and imaging guided tumor surgery.

In vitro imaging demonstrated strong molecular selectivity of CH1055-affibody molecule to EGFR+ cancer cells. The conjugate was then intravenously injected (60 μg) into immunodeficient mice (n=3) with xenograft human squamous cell carcinoma tumors. The tumor fluorescence was clearly observed 1 hour PI (1200LP, 300 ms) and within 6 hours, the T/NT reached ~15. This resulted in a 5-fold boost over previous results that utilized NIR-I fluorophores for molecular imaging with the same affibody molecule.(23, 33)'(34) Specific in vivo tumor targeting was verified by injecting a blocking dose of the anti-EGFR affibody molecule concurrently with the CH1055-affibody molecule. In this case very low levels of tumor fluorescence were observed due to affibody molecule blocking. At 6 hours post injection of CH1055-affibody molecule, we performed the first NIR-II imaging guided tumor excision surgery and observed very clear differentiation between cancerous and healthy tissue owing to the high T/NT ratio (FIG. 7) In FIG. 7, the horizontal line indicates the T/NT obtained with NIR-I flurophore used in conjunction with the same anti-EGFR affibody.

Example 8

Photoacoustic Enhancement

As a newly emerging technique in biomedical imaging, photoacoustic enhancement overcomes the depth and resolution limits of conventional optical imaging techniques and provides strong optical absorption contrast and high ultrasonic resolution. Further details on photoacoustic enhancement as used here may be found in "Photoacoustic contrast agent based active ultrasound imaging," US 20120203103. As described there, Photoacoustic (PA) imaging is a noninvasive imaging technique that may be used in medical environments, e.g., to detect, inter alia, vascular disease, skin abnormalities and some types of cancer. PA imaging generally involves flashing a laser at low energy with a near-infrared wavelength onto a target area or region. Infrared light penetrates relatively deeply into the body. This creates a large radiated area for a more detailed picture.

Figure 8A:
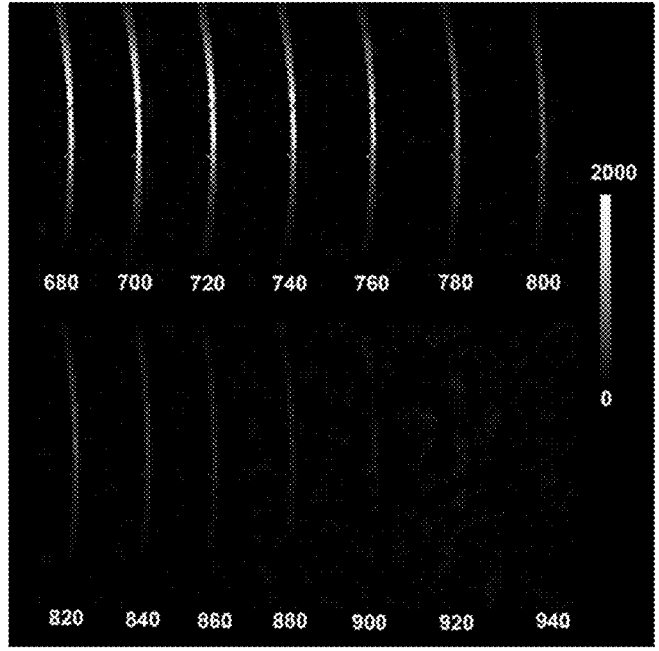
FIG. 8A, 8B, 8C is a set of images and graphs showing the photoacoustic signal of CH1055 at different excitation wavelengths and concentrations.
Figure 8B:
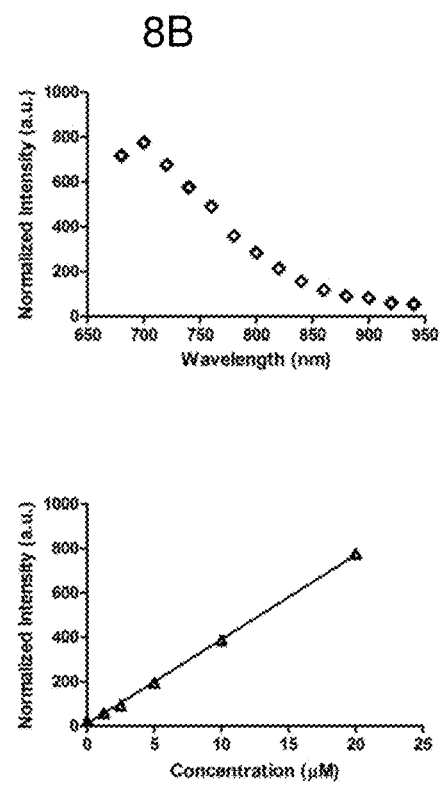
Figure 8C:
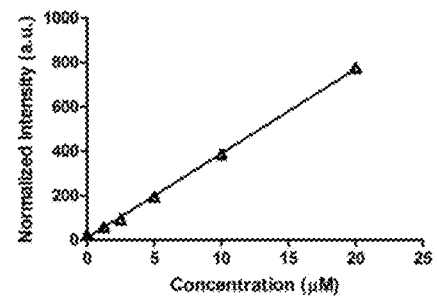

Fluorophores with the present design not only have NIR II fluorescence, but also show strong absorption in the NIR-I region and show promise for in vivo photoacoustic imaging. As described previously, CH1055 molecules are structured with tertiary amine group (as an electron donor, High-lying HOMO) and beno[1,2,5]thioladiazole group (as an electron acceptor, low-lying LUMO) linked through conjugated units. By changing the donor, acceptor, and π spacer, CH1055 absorption and emission can be tuned within both NIR-I and NIR-II windows (600-1600 nm). CH1055 molecules have NIR-I absorption with maximum at 700 nm. With strong absorption in the NIR-I region, CH1055 efficiently generated photoacoustic signals following NIR pulsed laser irradiation (FIG. 8A). The maximum photoacoustic signal of CH1055 was observed at 700 nm (FIG. 8B), which was very close to their maximum absorption wavelength. The photoacoustic amplitude of CH1055 at 700 nm was determined at different concentrations, displaying a linear relationship between photoacoustic signal and concentration (FIG. 8C).

Example 9

Photothermal Effects and Therapy

The present compounds may be used to produce beneficial photothermal effects, e.g. in tumors in vivo. Further details of this approach may be found in Hirsh et al, "Nanoshell-mediated near-infrared thermal therapy of tumors under magnetic resonance guidance," Proc. Nat. Acad. Sci. 100(23): 1349-13554 (2003) and WO2013186735, "Photothermal detection."

Figure 9:
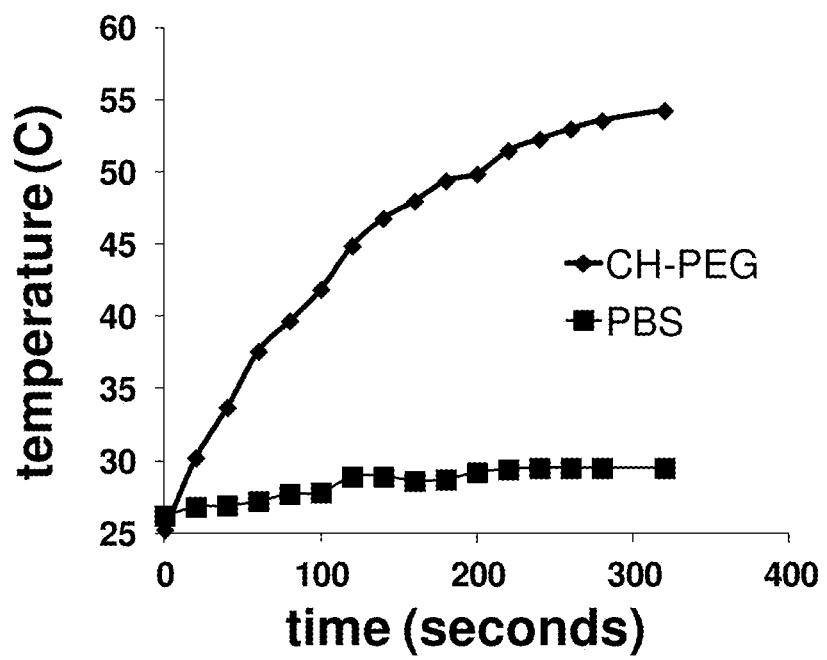
FIG. 9 is a graph showing the photothermal effect of CH1055-PEG.

To study the photothermal properties of CH1055-PEG in vitro, the compound solution and phosphate buffered saline (PBS) were irradiated and measured for 1 min., 2 min., 3 min., 4 min and 5 min. The temperature signature increased in a time dependent manner and was measures in a range centered about 36-44 deg. C. (data not shown). The temperature of the probe solution rose rapidly, reaching an average temperature of 54° C. after irradiation for 300 seconds (FIG. 9), making it useful for the photothermal treatment of solid tumors. In comparison, when PBS was irradiated under the same NIR light conditions, the temperature increased by only 4° C. These results clearly demonstrated that the NIR optical absorbance of the probe can be converted to thermal energy. CH1055-PEG provides good photothermal effects and can be used as an efficient NIR light absorber for the PTT of tumors.

In photothermal therapy, a dye such as described here is administered to a subject, and near-infrared is used to excite the dye and sensitize the target tissue. As described in the above-cited WO 2013186735, a laser may be directed to the tissue of interest, such as tumor cells or degenerative tissue. Heating them even by a few degrees and inspecting them with infra red (IR) camera can allow high quality detection of the boundaries of the tumor. As described in Hirsch et al., supra, near-infrared therapy may be carried out by delivering a therapeutic dose of heat to tumors under magnetic resonance guidance. In that paper, human breast carcinoma cells incubated with nanoshells in vitro were found to have undergone photothermally induced morbidity on exposure to NIR light (820 nm, 35 W/cm2).

The present dyes are coupled to nanoparticles (NPS) such as nanotubes, described above. As described in Mealncon, "Cancer Theranostics with Near-Infrared Light-Activatable Multimodal Nanoparticles," Acc. Chem. Res., 2011, 44 (10), pp 947-956, the present dyes, coupled with NPS, will home in solid tumors, either with or without a targeting mechanism, and the NIR light will induce a temperature rise in the cells. As a result, the temperature in the treatment volume is elevated above the thermal damage threshold, which kills the cells.

Example 10

Taurine or Sulfonic Acid Derivitized Compound CH-4T

This compound is also identified above in Example 1 as CH1055-4Taurine and is termed here CH-4T for short.

This compound is a highly water soluble NIR-II fluorophore with a dramatically increased quantum yield in serum. The compound contains a taurine (2-aminoethanesulfonic acid) group at the carboxyl linkers of CH1055. The four terminal sulfonic acid functional groups were found to further increase the aqueous solubility of the organic dye. Sulfonating the present NIR-II dyes is a general procedure that can be applied to a number of the NIR-II small molecules described above to increase their solubility. Data have demonstrated that CH-4T significantly brightens in serum through interactions with plasma proteins in a similar manner as ICG. CH-4T is highly soluble in both water and PBS and a ~15-fold increase in brightness is observed when compared to CH1055-PEG in serum. While fetal bovine serum (FBS) has been predominantly used experimentally, CH-4T demonstrates even further fluorescence enhancement in human serum.

Figure 10:
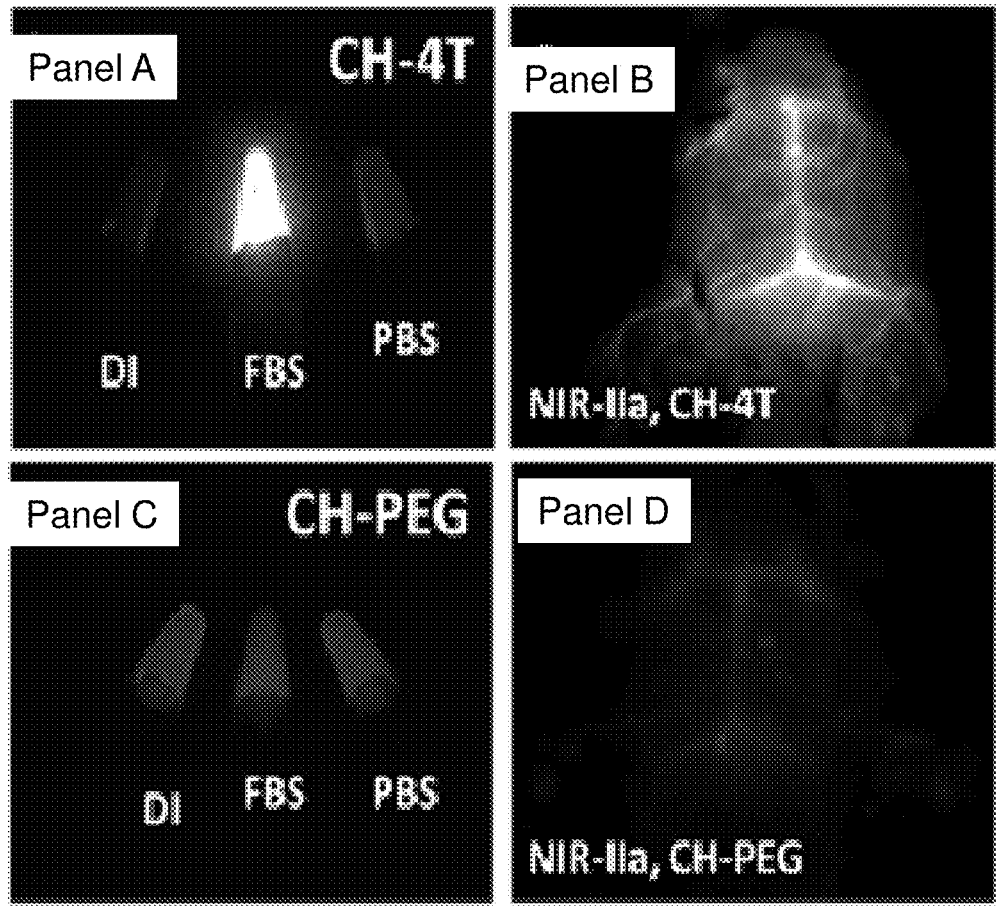
FIG. 10 is an image of fluorescent NIR-II images (1100 LP, 50 ms) of CH-4T (Panel A and Panel B) and CH1055-PEG (Panel C and Panel D) mixed with DI, FBS, and PBS. The absorbance value of both fluorophores (OD 0.02) in each respective media is equivalent at the excitation wavelength (808 nm) to compare relative quantum yields.
Figure 11:
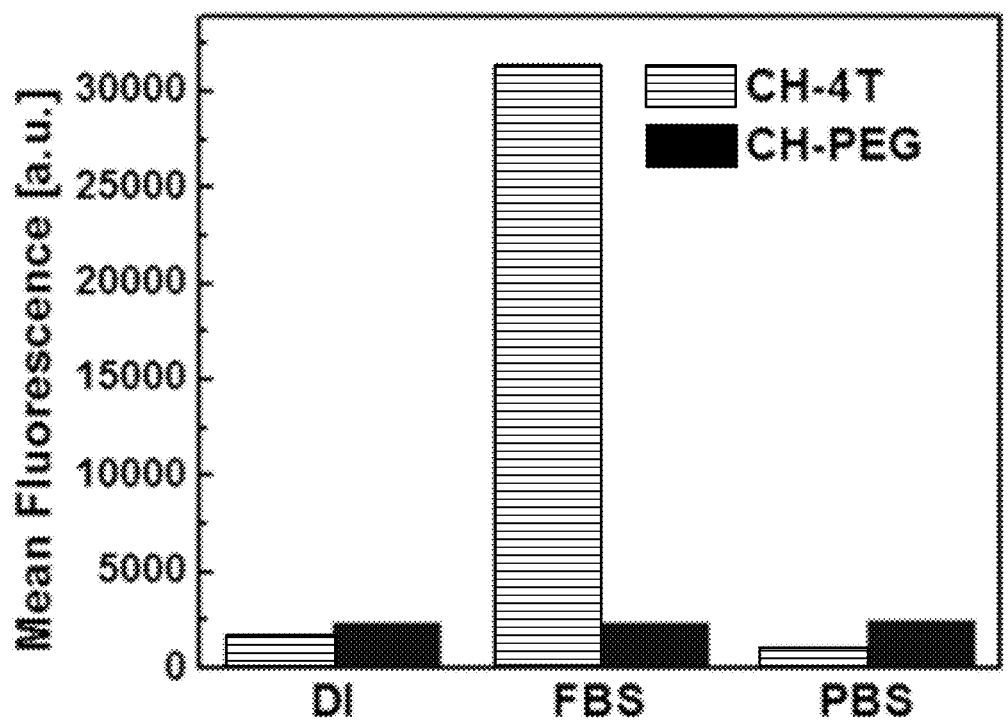
FIG. 11 is a graph showing ROI (region of interest) fluorescent intensity of each vial for both fluorophores in each media.

FIG. 10 shows a fluorescent NIR-II image (1100 LP, 50 ms) of CH-4T (Panel A) and CH1055-PEG (Panel C) mixed with DI (distilled water), FBS (fetal bovine serum), and PBS (phosphate buffered saline). The absorbance value of both fluorophores (OD 0.02) in each respective media is equivalent at the excitation wavelength (808 nm) to compare relative quantum yields. NIR-IIa fluorescent image of a C57 mouse brain (1300 LP) after an intravenous injection of equivalent doses of CH-4T (200 ms exposure; Panel B) and of CH1055-PEG (1 s exposure; Panel D). The image intensity scales have been compensated to account for the differences in the exposure times needed to clearly resolve brain vasculature. Related FIG. 11 shows ROI (region of interest) fluorescent intensity of each vial for both fluorophores in each media.

Further, the binding of CH-4T to serum proteins indicates strong binding to both human and bovine albumin, serum and whole blood of animals, as well as high-density lipoprotein (HDL) in conjunction with other fat solubilizing proteins. The integrated intensity showed a maximum of about $10^6$ for CH-4T in HS, integrated intensity was measured for CH-4T in FBS, CH-4T in BSA, and CH-4T in HAS, respectively. Significantly less intensity was shown for CH-4T in PBS, CH-PEG in FBS and CH-PEG PBS. This fluorescence enhancement produces a serum quantum yield of up to ~10% which is on par with ICG and is among the highest quantum yields of all NIR-II fluorophores (including carbon nanotubes). While soluble in PBS, the quantum yield of CH-4T was determined to be ~0.07%, yet is enhanced ~60× through complexation with serum proteins in FBS. This increase in brightness demonstrates the effect of applying taurine to the CH1055 core structure. These results may be expected with similar structural derivatives described here. Superior results for in vivo imaging applications can be predicted from data such as described above. It was also found that fluorescence enhancement increased up to 16 fold as the human serum albumin (HSA) concentration is increased up to around 2 µM when keeping [CH-4T] at a constant 1 µM (data not shown).

Sulfonated dyes as described here may be complexed in vitro to serum proteins to provide a quantum yield (fraction of photons absorbed resulting in emission of fluorescence) compared with an equivalent non-complexed dye. The sulfonated dye, is mixed with human serum albumin (commercially available from, e.g. Sigma-Aldrich, CAS No. 70024-90-7), bovine serum albumin (commercially available from e.g. Sigma-Aldrich, CAS No. 9048-46-8), Lipoprotein, high density from human plasma (commercially available from e.g. Sigma-Aldrich L1567), and fetal bovine serum (Sigma Aldrich F2442). The serum protein or proteins of interest may be incubated, as described above for a short time (e.g. ~10 min.) with sonication. The complexed dye is then separated from the serum protein used by any suitable physical method, such as centrifugation.

The excretion kinetics of CH-4T now resemble that of ICG after preliminary animal imaging as altering the terminal functional groups will naturally change the dye's biodistribution and excretion profile. These results indicate that the sulfonated CH-4T complexed with proteins in serum and blood is the brightest NIR-II contrast agent for in vivo use. It is a small molecule dye similar to ICG, Cy5, and IR800, and enables easier access to NIR-II imaging, as it doesn't require a specialized knowledge of nanomaterials which make up the majority of NIR-II fluorophores.

Increased brightening of CH-4T also results from protein interactions. A fluorescence emission spectrum of CH1055-PEG and CH-4T in both FBS and PBS was determined. The intensity for CH-4T in FBS was significantly higher than CH-4T in PBS, CH PEG in PBS or CH-PEG in FBS. The intensity for CH-4T/PBS, CH-PEG/PBS and CH-PEG/FBS all showed an intensity below 5,000 a.u. The increased intensity (40,000 a.u. around 1000 nm) for CH-4T in FBS was observed.

While CH-4T complexed with proteins produces an incredibly bright contrast agent, pretreatment of the proteins prior to complexation and subsequent isolation of the bright dye-protein complexes can introduce a further increase in brightness. For instance, a short 10 minutes of horn sonication of FBS prior to mixing with CH-4T followed by 10 minutes of heating in a hot water bath at ~80° C. can boost the brightness of the CH-4T-protein complex by ~3-4-fold. The effects on the fluorescence emission spectrum of heating and pre-horn sonicating can be seen while the brightness difference of an FBS-CH-4T solution before and after treatment (data not shown). In this experiment, the greatest intensity increase was observed with the CH-4T in sonicated FBS and heated at 80° C. Increases were also seen, to a lesser extent, with CH-4T in FBS with heating to 80° C., CH-4T in sonicated FBS, and CH-4T in FBS.

This increase in brightness with treated FBS produces the first NIR-II high quantum yield fluorophore with a quantum yield of ~13% which is 30× higher than carbon nanotubes. This is a general procedure that can be applied to any protein that demonstrates enhancement when mixed with CH-4T. Pre-horn sonication and heating of HSA, BSA, and FBS with CH-4T have all shown an increase in brightness post-treatment. The order of brightness follows the same order as the enhancement of each protein-dye complex prior to treatment.

After optimizing the conditions to produce the CH-4T-protein complexes with the highest NIR-II brightness, a simple density gradient ultracentrifugation (DGU) step can be employed to isolate the brightest dye-protein complexes. Density gradient ultracentrifugation is a separation technique that involves the creation of a linearly changing density gradient along the length of the centrifuge tube. The CH-4T in treated FBS is added above the density gradient and during ultracentrifugation, the dye-protein complex migrates to the position within the gradient where the buoyant density of the complex matches that of the surrounding gradient. This procedure allows the isolation of the highly fluorescent CH-4T complexes that can be extracted and used for in vivo NIR-II imaging. While the exact quantum yield of the dye-protein complex post-DGU has not yet been measured, one should expect a notable increase after the dimmer CH-4T protein fragments have been removed. Further work will be performed to quantify the optical properties of these CH-4T-protein complexes post-DGU as their brightness seems likely to produce the first ultra-high quantum yield NIR-II fluorophore.

In addition to being a useful contrast agent for the visualization of lymph nodes and blood vasculature, these CH-4T complexes can be used as scaffolding for the conjugation of targeting ligands. For instance, after DGU, the brightest complexes can be isolated and with bioconjugation techniques, tumor-targeting ligands such as antibodies and peptides can be attached to these complexes to produce imaging agents that can selectively accumulate in tumors. The high quantum yield of these dye-protein fragments will allow for ultra-high signal-to-background ratios during precise tumor targeting.

CONCLUSION

The above specific description is meant to exemplify and illustrate the method and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

REFERENCES

1. L. P. Kamolz, H. Andel, T. Auer, G. Meissl, M. Frey, Evaluation of skin perfusion by use of Indocyanine green video angiography: Rational design and planning of trauma surgery. *J. TRAUMA* 61, 635-641 (2006).
2. D. H. Orth, A. Patz, R. W. Flower, Potential Clinical Applications of Indocyanine Green Choroidal Angiography—Preliminary-Report. *Eye Ear Nose Throat Mon.* 55, 4-11 (1976).
3. H. S. Choi et al., Targeted zwitterionic near-infrared fluorophores for improved optical imaging. *Nat. Biotechnol.* 31, 148-153 (2013).
4. S. Gioux, H. S. Choi, J. V. Frangioni, Image-Guided Surgery Using Invisible Near-Infrared Light: Fundamentals of Clinical Translation. *Mol. Imaging* 9, 237-255 (2010).
5. G. Hong et al., Multifunctional in vivo vascular imaging using near-infrared II fluorescence. *Nat. Med.* 18, 1841-1846 (2012).
6. Z. Liu et al., In vivo biodistribution and highly efficient tumour targeting of carbon nanotubes in mice. *Nat. Nanotechnol.* 2, 47-52 (2007).

7. A. L. Vahrmeijer, M. Hutteman, J. R. van der Vorst, C. J. van de Velde, J. V. Frangioni, Image-guided cancer surgery using near-infrared fluorescence. *Nat. Rev. Clin. Oncol.* 10, 507-518 (2013).
8. G. Hong et al., In Vivo Fluorescence Imaging with Ag2S Quantum Dots in the Second Near-Infrared Region. *Angew. Chem. Int. Ed.* 124, 9956-9959 (2012).
9. G. S. Hong et al., Ultrafast fluorescence imaging in vivo with conjugated polymer fluorophores in the second near-infrared window. *Nat. Commun.* 5 (2014).
10. S. Diao et al., Chirality Enriched (12,1) and (11,3) Single-Walled Carbon Nanotubes for Biological Imaging. *J. Am. Chem. Soc.* 134, 16971-16974 (2012).
11. K. Welsher, S. P. Sherlock, H. J. Dai, Deep-tissue anatomical imaging of mice using carbon nanotube fluorophores in the second near-infrared window. *Proc. Natl. Acad. Sci. U.S.A.* 108, 8943-8948 (2011).
12. G. Hong, Diao, S., Chang, J, Antaris, A. L., Chen, C., Zhang, B., Zhao, S., Atochin, D. N., Huang, P. L., Andreasson, K. L., Kuo, C. J., Dai, H., Through-skull fluorescence imaging of the brain in a new near-infrared window. *Nat Photon.* (2014).
13. H. S. Choi et al., Renal clearance of quantum dots. *Nat. Biotechnol.* 25, 1165-1170 (2007).
14. Z. Liu et al., Circulation and long-term fate of functionalized, biocompatible single-walled carbon nanotubes in mice probed by Raman spectroscopy. *Proc. Natl. Acad. Sci. U.S.A.* 105, 1410-1415 (2008).
15. A. L. Antaris et al., Ultra-Low Doses of Chirality Sorted (6,5) Carbon Nanotubes for Simultaneous Tumor Imaging and Photothermal Therapy. *ACS Nano* 7, 3644-3652 (2013).
16. K. Welsher et al., A route to brightly fluorescent carbon nanotubes for near-infrared imaging in mice. *Nat. Nanotechnol.* 4, 773-780 (2009).
17. J. A. J. Fitzpatrick et al., Long-term Persistence and Spectral Blue Shifting of Quantum Dots in Vivo. *Nano Lett.* 9, 2736-2741 (2009).
18. S. T. Yang et al., Long-term accumulation and low toxicity of single-walled carbon nanotubes in intravenously exposed mice. *Toxicol. Lett.* 181, 182-189 (2008).
19. Z. M. Tao et al., Biological Imaging Using Nanoparticles of Small Organic Molecules with Fluorescence Emission at Wavelengths Longer than 1000 nm. *Angew. Chem. Int. Ed.* 52, 13002-13006 (2013).
20. S. Kim et al., Near-infrared fluorescent type II quantum dots for sentinel lymph node mapping. *Nat. Biotechnol* 22, 93-97 (2004).
21. H. Maeda, J. Wu, T. Sawa, Y. Matsumura, K. Hori, Tumor vascular permeability and the EPR effect in macromolecular therapeutics: a review. *J. Control Release* 65, 271-284 (2000).
22. G. C. Wishart, S. W. Loh, L. Jones, J. R. Benson, A feasibility study (ICG-10) of indocyanine green (ICG) fluorescence mapping for sentinel lymph node detection in early breast cancer. *Eur. J. Surg. Oncol.* 38, 651-656 (2012).
23. J. H. Gao et al., Affibody-based nanoprobes for HER2-expressing cell and tumor imaging. *Biomaterials* 32, 2141-2148 (2011).
24. G. Qian et al., Band Gap Tunable, Donor-Acceptor-Donor Charge-Transfer Heteroquinoid-Based Chromophores: Near Infrared Photoluminescence and Electroluminescence. *Chem. Mater.* 20, 6208-6216 (2008).
25. A. T. R. Williams, S. A. Winfield, J. N. Miller, Relative Fluorescence Quantum Yields Using a Computer-Controlled Luminescence Spectrometer. *Analyst.* 108, 1067-1071 (1983).
26. S. Y. Ju, W. P. Kopcha, F. Papadimitrakopoulos, Brightly Fluorescent Single-Walled Carbon Nanotubes via an Oxygen-Excluding Surfactant Organization. *Science* 323, 1319-1323 (2009).
27. M. E. Fox, F. C. Szoka, J. M. J. Frechet, Soluble Polymer Carriers for the Treatment of Cancer: The Importance of Molecular Architecture. *Acc. Chem. Res.* 42, 1141-1151 (2009).
28. S. L. Troyan et al., The FLARE Intraoperative Near-Infrared Fluorescence Imaging System: A First-in-Human Clinical Trial in Breast Cancer Sentinel Lymph Node Mapping. *Ann. Surg. Oncol.* 16, 2943-2952 (2009).
29. C. W. Chi et al., Use of Indocyanine Green for Detecting the Sentinel Lymph Node in Breast Cancer Patients: From Preclinical Evaluation to Clinical Validation. *PLOS ONE* 8 (2013).
30. E. Tanaka, H. S. Choi, H. Fujii, M. G. Bawendi, J. V. Frangioni, Image-guided oncologic surgery using invisible light: Completed pre-clinical development for sentinel lymph node mapping. *Ann. Surg. Oncol.* 13, 1671-1681 (2006).
31. M. Gurfinkel et al., Pharmacokinetics of ICG and HPPH-car for the detection of normal and tumor tissue using fluorescence, near-infrared reflectance imaging: A case study. *Photochem. Photobiol.* 72, 94-102 (2000).
32. M. Zimmermann, A. Zouhair, D. Azria, M. Ozsahin, The epidermal growth factor receptor (EGFR) in head and neck cancer: its role and treatment implications. *Radiat. Oncol.* 1 (2006).
33. Z. Miao, G. Ren, H. G. Liu, L. Jiang, Z. Cheng, Cy5.5-labeled Affibody molecule for near-infrared fluorescent optical imaging of epidermal growth factor receptor positive tumors. *J. Biomed. Opt.* 15 (2010).
34. S. B. Qi et al., Evaluation of Four Affibody-Based Near-Infrared Fluorescent Probes for Optical Imaging of Epidermal Growth Factor Receptor Positive Tumors. *Bioconjugate Chem.* 23, 1149-1156 (2012).
35. X. X. He, J. H. Gao, S. S. Gambhir, Z. Cheng, Near-infrared fluorescent nanoprobes for cancer molecular imaging: status and challenges. *Trends Mol. Med.* 16, 574-583 (2010).

What is claimed is:

1. A method of synthesizing a near-infrared-II fluorophore, comprising:
   a) synthesizing a dialkyl 3,3'((arylazanediyl)bis(4,1-phenylene))diacrylate with a reagent of formula Ph$_3$PCHCO$_2$(alkyl);
   b) synthesizing a dialkyl 3,3'((arylazanediyl)bis(4,1-phenylene))propionate from the compound of step a) using hydrogen and a catalyst;
   c) halogenating the arylazanediyl group of the compound of step b);
   d) protecting two propionate groups of the compound of step c) with a protecting reagent comprising a trimethylsilyl (TMS) group;
   e) substituting the halogen of the compound of step d) with a coupling group;
   f) reacting a 2,1,3-benzothiodiazole-containing compound with the coupling group of the compound of step e) such that in the resulting compound a 2,1,3-benzothiodiazole-containing group is coupled to two protected dialkyl 3,3'((arylazanediyl)bis(4,1-phenylene)) propionate groups;
   g) reacting the compound of step f) such that the 2,1,3-benzothiodiazole-containing group of the resulting compound has one more ring than the 2,1,3-benzothiodiazole-containing group of the compound of step f);
   h) deprotecting the two protected propionate groups of the compound of step g).

2. The method of claim 1, wherein the arylazanediyl group is a phenylazanediyl group.

3. The method of claim 1, further comprising: i) attaching an amino-containing group to the compound of step h) by reacting an amino-containing compound with a propionate group of the compound of step h).

4. The method of claim 3, wherein the amino-containing compound comprises a sulfonic acid group.

5. The method of claim 4, wherein the amino-containing compound comprises a taurinyl group.

6. The method of claim 3, wherein step i) involves hexafluorophosphate benzotriazole tetramethyl uronium (HBTU).

7. The method of claim 3, wherein the amino-containing compound contains a polyethylene glycolyl group.

8. The method of claim 3, wherein the amino-containing compound is an affibody.

9. The method of claim 3, wherein the affibody is an anti-EGFR affibody.

10. The method of claim 1, wherein step a) involves alkyl (triphenylphosphoranylidene)acetate.

11. The method of claim 1, wherein the halogenation is bromination.

12. The method of claim 1, wherein step d) involves N,N'-dicyclohexylcarbodiimide (DCC).

13. The method of claim 1, wherein the 2,1,3-benzothiodiazole compound has a nitro group at each of the 5 and 6 positions.

14. The method of claim 1, wherein step f) is a Suzuki coupling.

15. The method of claim 1, wherein the coupling group is a pinacolboranyl group.

16. The method of claim 1, wherein step g) involves N-sulfinylaniline (PNSO).

* * * * *

UNITED STATES PATENT AND TRADEMARK OFFICE
CERTIFICATE OF CORRECTION

PATENT NO. : 10,894,121 B2
APPLICATION NO. : 16/186947
DATED : January 19, 2021
INVENTOR(S) : Zhen Cheng et al.

It is certified that error appears in the above-identified patent and that said Letters Patent is hereby corrected as shown below:

In the Specification

In Column 19, Line 36:
Delete "MM" and replace with --MRI--.

In Column 21, Line 51:
Delete "Synthesis of C111055, C111055-PEG, C111055-4" and replace with --Synthesis of CH1055, CH1055-PEG, CH1055-4--.

In Column 21, Line 52:
Delete "Taurine and C111055-3 Taurine" and replace with --Taurine and CH1055-3 Taurine--.

In Column 33, Line 56:
Delete "(trimethylsilylpethyl)" and replace with --(trimethylsilyl)ethyl)--.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*